US012811016B1

(12) United States Patent
Donnella et al.

(10) Patent No.: US 12,811,016 B1
(45) Date of Patent: Nov. 24, 2026

(54) GENERATING A MULTI-ENTITY GRAPH REPRESENTATION FOR DETERMINING A THERAPEUTIC TREATMENT UTILIZING A GRAPH NEURAL NETWORK

(71) Applicant: Recursion Pharmaceuticals, Inc., Salt Lake City, UT (US)

(72) Inventors: Hayley Jeton Donnella, Austin, TX (US); Hemanth Kanakamedala, Montclair, NJ (US); Seyed Ali Madani Tonekaboni, Toronto (CA); William Paul Bone, Salt Lake City, UT (US)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 19/287,438

(22) Filed: Jul. 31, 2025

(51) Int. Cl.
*G16H 50/70* (2018.01)
*G06N 3/042* (2023.01)
*G06N 3/08* (2023.01)
*G16H 20/10* (2018.01)

(52) U.S. Cl.
CPC ............. *G16H 50/70* (2018.01); *G06N 3/042* (2023.01); *G06N 3/08* (2013.01); *G16H 20/10* (2018.01)

(58) Field of Classification Search
CPC ........ G16H 50/70; G16H 20/10; G06N 3/042; G06N 3/08
See application file for complete search history.

(56) References Cited

U.S. PATENT DOCUMENTS 12,119,090 B1 10/2024 Kraus et al.
2022/0005608 A1* 1/2022 Koo ....................... G16H 50/20
2022/0188659 A1* 6/2022 Krasnoslobodtsev ... G06N 3/08
2023/0084203 A1* 3/2023 Li ........................ G06N 3/0499 706/25
2023/0386612 A1* 11/2023 Frings .................... G16H 50/70
2024/0160904 A1* 5/2024 Zhu ....................... G08G 1/0145
2024/0303533 A1* 9/2024 Seth ....................... G06N 20/00
(Continued)

OTHER PUBLICATIONS

Li et al. (Graph Representation Learning in Biomedicine, Jun. 2022, p. 1-S18) (Year: 2022).*
(Continued)

*Primary Examiner* — George Giroux
(74) *Attorney, Agent, or Firm* — Keller Preece PLLC

(57) ABSTRACT

The present disclosure relates to methods, systems, and non-transitory computer-readable media for utilizing novel multi-entity graph representations and a graph neural network to determine therapeutic treatments for clinical patients and/or to select preclinical models that are representative of a patient population. In particular, the disclosed systems can access (or receive) data from a plurality of data sources, including digital clinical datasets, functional response machine learning embeddings, and/or digital preclinical-model datasets. Based on this data, the disclosed systems may generate a multi-entity graph representation that includes a plurality of nodes corresponding to a plurality of data entity types (e.g., clinical patients, genes, compounds, and/or preclinical models) and a plurality of edges that connect the plurality of nodes. In some cases, the disclosed systems generate embeddings (e.g., node embeddings) in a latent space utilizing the graph neural network and compare the embeddings to determine a therapeutic treatment and/or select a preclinical model.

20 Claims, 10 Drawing Sheets

(56) References Cited

U.S. PATENT DOCUMENTS

| | | | | |
|---|---|---|---|---|
| 2024/0303544 | A1* | 9/2024 | Baranzini | G06N 5/022 |
| 2024/0404700 | A1* | 12/2024 | Trakadis | G16H 50/20 |
| 2024/0420849 | A1* | 12/2024 | Gueret | G16H 10/60 |
| 2025/0182841 | A1* | 6/2025 | Fisher | G16B 15/30 |
| 2025/0218538 | A1 | 7/2025 | Selega et al. | |
| 2025/0290843 | A1* | 9/2025 | Laing | G16B 40/20 |
| 2025/0305026 | A1* | 10/2025 | Coskun | G16B 15/00 |

OTHER PUBLICATIONS

Nelson et al. (Integrating biomedical research and health records to create knowledge-based biologically meaningful machine-readable embeddings, Jul. 2019, pp. 1-10) (Year: 2019).*

* cited by examiner

GENERATING A MULTI-ENTITY GRAPH REPRESENTATION FOR DETERMINING A THERAPEUTIC TREATMENT UTILIZING A GRAPH NEURAL NETWORK

BACKGROUND

Recent years have seen significant improvements in computational methods for analyzing biomedical data to support therapeutic treatment determinations or patient stratification. For example, conventional systems can apply statistical models or machine learning algorithms to analyze clinical variables or molecular profiles in isolation and for specific data entity types (e.g., clinical patients or preclinical models). To illustrate, some systems may predict a therapeutic treatment for a clinical patient based solely on structured clinical patient data, while others may associate gene perturbations with compound sensitivity using only preclinical models. Although there have been some developments in these areas, existing systems nevertheless exhibit a number of deficiencies or drawbacks, particularly relating to flexibility, efficiency, and their technical processes for determining a therapeutic treatment for a clinical patient.

These along with additional problems and issues exist with regard to conventional systems.

SUMMARY

This disclosure describes one or more embodiments of methods, systems, and non-transitory computer-readable storage media that provide benefits and/or solve one or more of the foregoing and other problems in the art by utilizing novel multi-entity graph representations and a graph neural network to determine therapeutic treatments-including patient stratifications—for clinical patients and/or select preclinical models that are representative of a patient population. In particular, the disclosed systems can access (or receive) data from a plurality of data sources, including a digital clinical dataset, functional response machine learning embeddings, and/or a digital preclinical-model dataset (e.g., a dataset associated with preclinical models, such as xenografts, organoids, or cell lines). Based on this data, the disclosed systems may generate a multi-entity graph representation that includes nodes corresponding to a plurality of data entity types, such as a clinical patient, a gene, a compound, and/or a preclinical model. The disclosed systems may also generate a plurality of edges to connect the nodes within the same multi-entity graph representation. In some embodiments, the disclosed systems utilizes a graph neural network (e.g., a graph attention model) to process the multi-entity graph representation and generate embeddings (e.g., node embeddings, edge embeddings, and/or multi-entity graph representation embeddings) in a new latent space that enables comparison of the plurality of data entity types. Indeed, by comparing the embeddings, the disclosed systems may determine a therapeutic treatment for one or more clinical patients and/or select a preclinical model that is representative of a patient population. Similarly, the disclosed systems can compare embeddings to determine similarities between perturbations or other nodes such as compounds and/or genes, patients, preclinical models, etc. These similarities can be used to improve technical drug discovery pipelines and/or therapeutic treatment processes. Additional features and advantages of one or more embodiments of the present disclosure are outlined in the description which follows, and in part will be obvious from the description, or may be learned by the practice of such example embodiments.

BRIEF DESCRIPTION OF THE DRAWINGS

The detailed description provides one or more embodiments with additional specificity and detail through the use of the accompanying drawings, as briefly described below.

DETAILED DESCRIPTION

Figure 1:
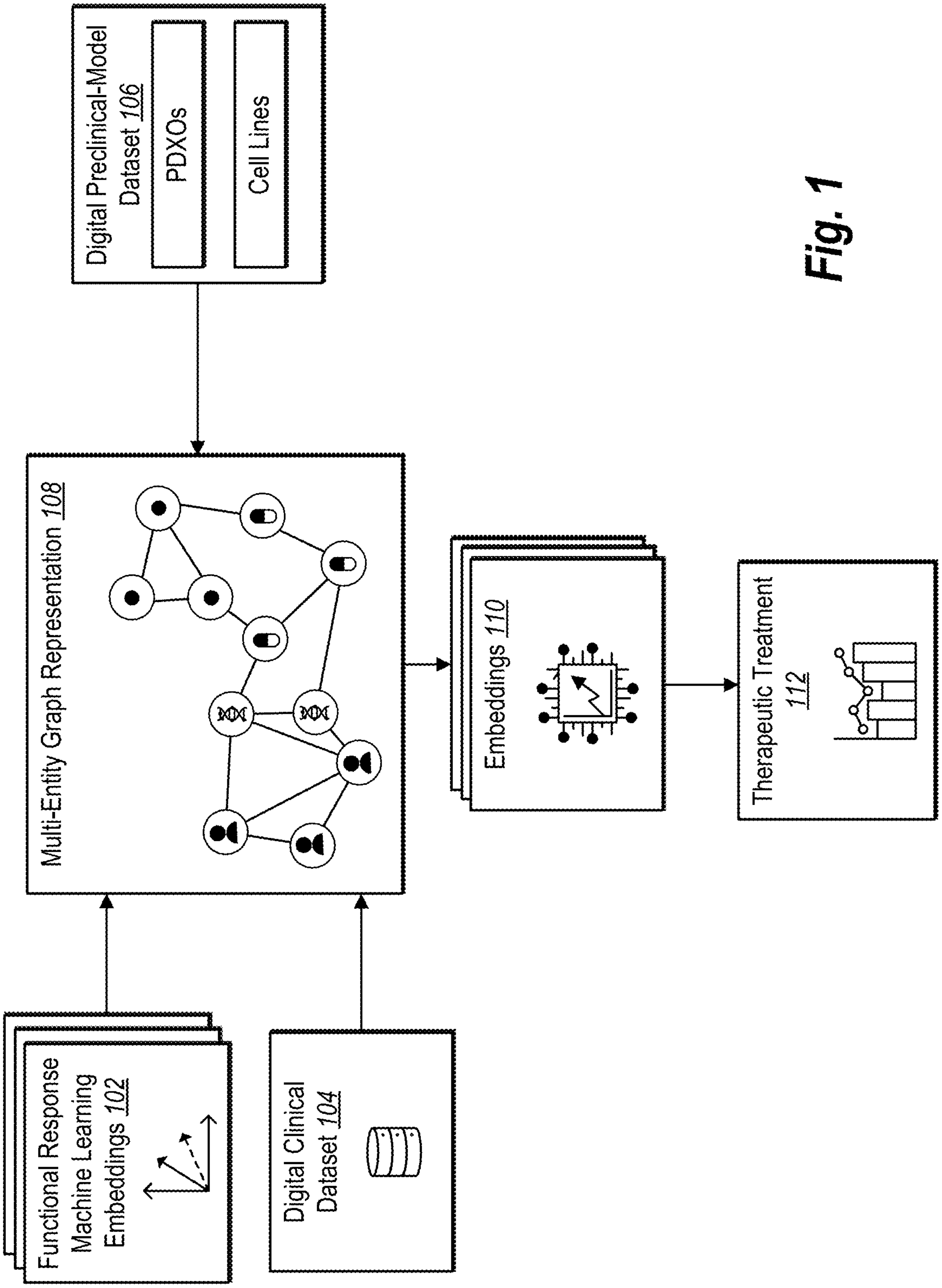
FIG. 1 illustrates an example overview of determining a therapeutic treatment for one or more patients utilizing a multi-entity graph representation in accordance with one or more embodiments.

This disclosure describes one or more embodiments of a graph modeling system 100 that can utilize novel multi-entity graph representations and a graph neural network to determine therapeutic treatments-including patient stratifications—for clinical patients, improve drug discovery pipelines, and/or select preclinical models that are representative of a patient population. In particular, the graph modeling system 100 can access (or receive) data from a plurality of data sources, including a digital clinical dataset, functional response machine learning embeddings, and/or a digital preclinical-model dataset (e.g., a dataset associated with preclinical models, such as xenografts, organoids, or cell lines). Based on this data, the graph modeling system 100 may generate a multi-entity graph representation that includes nodes corresponding to a plurality of data entity types. To elaborate, the graph modeling system 100 may generate a patient node corresponding to a clinical patient, a compound node corresponding to a compound, a preclinical model node corresponding to a preclinical model, and/or a gene node corresponding to a gene. The graph modeling system 100 may also generate a plurality of edges to connect the nodes all within the same multi-entity graph representation. For example, the graph modeling system 100 may generate a patient-patient edge between the patient node and a second patient node, a patient-gene edge between the patient node and the gene node, a gene-gene edge between the gene node and a second gene node, a gene-compound edge between the gene node and the compound node, a preclinical model-gene edge between the preclinical model node and the gene node, and/or a preclinical model-preclinical model edge between the preclinical model node and a second preclinical model node.

In at least one embodiment, graph modeling system 100 utilizes a graph neural network (e.g., a graph attention model) to process the multi-entity graph representation and generate, in a new latent space, embeddings of the nodes, the plurality of edges, and/or of the multi-entity graph representation 108. For instance, the graph modeling system 100 may utilize the graph neural network to generate a clinical patient embedding, a compound embedding, a preclinical model embedding, and/or a gene embedding in the new latent space. In some cases, the graph modeling system 100 compares the embeddings to determine a therapeutic treatment for one or more clinical patients and/or to select a preclinical model that is representative of a patient population.

Further, in the same or other embodiments, the graph modeling system 100 trains (or fine-tunes) the graph neural network based on one or more multi-entity graph representations (e.g., utilizing a self-supervised training approach). To elaborate, the graph modeling system 100 may mask one or more edge weights of a subset of the plurality of edges of a multi-entity graph representation. The graph modeling system 100 may also utilize the graph neural network to generate predicted edge weights for the subset of the plurality of edges that were masked. In some cases, the graph modeling system 100 modifies one or more parameters of the graph neural network based on a determined loss between the edge weights of the multi-entity graph representation and the predicted edge weights. In at least one embodiment, the graph modeling system 100 iteratively performs these steps.

FIG. 1 illustrates an example overview of determining a therapeutic treatment for one or more patients utilizing a multi-entity graph representation in accordance with one or more embodiments. Additional detail regarding the various acts and processes introduced in relation to FIG. 1 is provided thereafter with reference to subsequent figures.

As illustrated in FIG. 1, the graph modeling system 100 generates a multi-entity graph representation 108 from a plurality of sources, including functional response machine learning embeddings 102, a digital clinical dataset 104, and/or a digital preclinical-model dataset 106. For instance, the graph modeling system 100 generates or identifies (e.g., from a functional response embedding store) functional response machine learning embeddings 102 for one or more genes (e.g., a target gene) and/or for one or more compounds. In particular, the graph modeling system 100 can utilize one or more models (e.g., machine learning models) to generate the functional response machine learning embeddings 102. For instance, the graph modeling system 100 can utilize a phenomic machine learning model to generate the functional response machine learning embeddings 102 that include phenomic embeddings (e.g., perturbation image embeddings) derived from one or more images of cells that have undergone a gene-specific perturbations (e.g., CRISPR gene knockout) and/or compound-specific perturbations. Additionally or alternatively, the graph modeling system 100 can utilize a transcriptomic machine learning model (e.g., a transcriptomics foundation model) to generate the functional response machine learning embeddings 102 that include transcriptomic embeddings derived from one or more gene expression profiles (transcriptomic profiles comprising RNA counts) corresponding to perturbed cellular states of cells.

As also illustrated in FIG. 1, the graph modeling system 100 accesses or receives data from the digital clinical dataset 104 for a plurality of clinical patients (e.g., having a disease such as cancer). For instance, the graph modeling system 100 can access or receive clinical trial data from the digital clinical dataset 104, including patient genetic data (e.g., DNA data and/or RNA data), clinical variables data, and/or clinical outcomes data. The graph modeling system 100 may also identify one or more features from the clinical trial data for generating clinical feature representations for the plurality of clinical patients. In some cases, the graph modeling system 100 can access or receive data from a plurality of digital clinical datasets for the plurality of clinical patients.

Additionally, as illustrated in FIG. 1, the graph modeling system 100 accesses or receives data from the digital preclinical-model dataset 106 for one or more preclinical models. In particular, the graph modeling system 100 may access or receive preclinical data associated with one or more preclinical models, such as cell lines, xenografts (e.g., patient-derived xenografts or PDXs), and/or organoids (e.g., patient-derived organoids or PDOs and/or patient-derived xenograft organoids or PDXOs). For instance, the graph modeling system 100 can access or receive preclinical model sensitivity data (e.g., preclinical model gene sensitivity data or preclinical model compound sensitivity data) of a preclinical model exposed to a perturbation. As an example, the graph modeling system 100 can access or receive preclinical model sensitivity data of a preclinical model exposed to a gene knockout of a gene and/or of a preclinical model exposed to a compound with respect to a gene. From the preclinical model sensitivity data, the graph modeling system 100 may identify (or determine) a gene expression metric and/or a compound-gene expression metric (e.g., transcriptomic profiles of the preclinical model resulting from the perturbation). Additionally, the graph modeling system 100 may identify one or more features (e.g., meta features) from the preclinical data for generating preclinical model feature representations for the one or more preclinical models. In some cases, the graph modeling system 100 can access or receive data from a plurality of digital preclinical-model datasets for the one or more preclinical models.

In one or more embodiments, the graph modeling system 100 may proactively address data limitations, such as missing data or inconsistencies. For example, to address data limitations, the graph modeling system 100 may implement data imputation techniques, such as automatically filling in missing values using statistical or machine learning methods and/or estimating missing values (e.g., using k-nearest neighbors or deep generative models). As another example, to address data limitations, the graph modeling system 100 may implement refining data acquisition strategies.

As further illustrated in FIG. 1, the graph modeling system 100 generates a multi-entity graph representation 108 that includes nodes and edges. In particular, the graph modeling system 100 may generate the nodes and/or edges of the multi-entity graph representation 108 based on the functional response machine learning embeddings 102, data from the digital clinical dataset 104, and/or data from the digital preclinical-model dataset 106. In at least one embodiment, the graph modeling system 100 generates the nodes for a plurality of data entities, with each being associated with a particular data entity type of a plurality of data entity types. To elaborate, the plurality of data entity types may include, for example, a clinical patient type, a compound type, a preclinical model type, and/or a gene type. In the same or other embodiments, the data entity types may additionally or alternatively include other biological entities or relationships, such as proteins or signaling pathways. In some cases, each node of the multi-entity graph representation 108 may include an identifiable vector of one or more features that determines (or identifies, specifies, or otherwise encodes identity characteristics of) the node type for each node. For instance, the graph modeling system 100 may generate a patient node corresponding to a particular clinical patient, a compound node corresponding to a particular compound, a preclinical model node corresponding to a particular preclinical model, and/or a gene node corresponding to a particular gene. Additionally or alternatively, the identifiable vector of features can identify or distinguish characteristics of a specific data entity.

In one or more embodiments, the graph modeling system 100 generates a plurality of edges for the multi-entity graph representation 108 that represent correlations between the nodes. In particular, the graph modeling system 100 may generate the plurality of edges by encoding relationships between the nodes into the edges. Moreover, the graph modeling system 100 can convert the plurality of edges to a common/normalized data schema such that the edges between different types of nodes are relatable across the multi-entity graph representation 108. In at least one embodiment, the graph modeling system 100 generates one or more differing edge types for the multi-entity graph representation 108 that connect the one or more differing node types. For example, the graph modeling system 100 may generate a patient-patient edge between a patient node and a second patient node, a patient-gene edge between a patient node and a gene node, a gene-gene edge between a gene node and a second gene node, a gene-compound edge between a gene node and a compound node, a preclinical model-gene edge between a preclinical model node and a gene node, and/or a preclinical model-preclinical model edge between a preclinical model node and a second preclinical model node. In the same or other embodiments, the graph modeling system 100 may generate one or more additional or alternative edges for the multi-entity graph representation 108, such as a preclinical model-compound edge and/or a compound-compound edge.

As shown in FIG. 1, the graph modeling system 100 generates embeddings 110 from the multi-entity graph representation 108. In particular, the graph modeling system 100 may generate the embeddings 110 based on the nodes and/or edges of the multi-entity graph representation 108 and/or based on the multi-entity graph representation 108 itself. For instance, the graph modeling system 100 may utilize a graph neural network (e.g., a graph attention model) to generate the embeddings 110 in a new latent space that enables comparison of the plurality of data entities corresponding to the nodes of the multi-entity graph representation 108 and/or of the relationships between the data entities corresponding to the edges of the multi-entity graph representation 108. Indeed, the graph modeling system 100 may generate a plurality of embeddings, including one or more of each of the following: a clinical patient embedding, a compound embedding, a preclinical model embedding, and/or a gene embedding.

As also shown in FIG. 1, the graph modeling system 100 determines a therapeutic treatment 112 for one or more patients of the plurality of clinical patients. In particular, the graph modeling system 100 may compare the embeddings 110 to determine the therapeutic treatment 112. For instance, the graph modeling system 100 may compare a clinical patient embedding to at least one of a compound embedding, a preclinical model embedding, a gene embedding and/or an additional clinical patient embedding. In some cases, the graph modeling system 100 performs the comparison to determine which patients of the plurality of clinical patients have a threshold level of similarity to a particular compound, preclinical model, gene, or another patient of the plurality of clinical patients. Based on the comparisons, the graph modeling system 100 may determine the therapeutic treatment 112, which may include determining a patient stratification of one or more patients of the plurality of clinical patients, a particular compound (e.g., drug) treatment for one or more patients of the plurality of clinical patients, and/or another therapeutic treatment for one or more patients of the plurality of clinical patients. Additionally or alternatively to determining the therapeutic treatment 112, the graph modeling system 100 may identify a preclinical model that is representative of a patient population.

Although FIG. 1 illustrates determining the therapeutic treatment 112, the graph modeling system 100 can utilize the embeddings 110 for a variety of purposes. For example, the graph modeling system 100 can compare the embeddings 110 for a variety of drug discovery purposes. To illustrate, the graph modeling system 100 can compare gene embeddings with other gene embeddings, gene embeddings with compound embeddings, and/or compound embeddings with other compound embeddings to determine possible targets for drug discovery (e.g., discover compounds that correspond to a gene known to impact cancer development or discover a new gene target that is similar to a compound or gene associated with cancer). The graph modeling system 100 can compare any of the embeddings in the multi-entity graph representation to generate biological interaction predictions between the various nodes.

As mentioned above, existing systems exhibit a number of technical deficiencies or drawbacks. For instance, existing systems are typically inflexible. Specifically, existing systems rigidly determine therapeutic treatments or identify representative preclinical models based on sparse amounts data that is often limited to a particular domain or data entity type, such as a clinical patient, a compound, or a preclinical model. For example, a system may consider only structured clinical variables for a patient or focus exclusively on gene perturbation profiles for preclinical models. These systems are commonly designed around fixed data schemas that do not accommodate integrating multiple types of biomedical data entities within a unified framework. As such, their architectures inherently constrain the types of inputs they can meaningfully incorporate.

In addition to (and in part due to) their inflexibilities, existing systems also exhibit deficiencies or drawbacks related to their process for determining a therapeutic treatment or for identifying a preclinical model. In particular, conventional approaches typically operate on isolated data siloes or domains-such as patient records, compound response datasets, or genetic perturbation screens-without modeling or leveraging the interconnections between data sources. As a result, such systems often process each data entity type independently, limiting their ability to infer complex cross-domain relationships that may be biologically or clinically relevant. This fragmented architecture restricts the system's ability to derive cohesive insights from heterogeneous data sources, thereby reducing the overall accuracy, precision, and reliability of treatment assignment or preclinical model selection.

Further, due in part to their inflexibilities and deficient processes, existing systems are also frequently inefficient. In particular, to circumvent their siloed natures, existing systems may attempt to utilize existing software to determine therapeutic treatments or to identify preclinical models. Yet, such existing software is often fragmented in nature, where each software application or web program is rigidly programmed to assess data associated with particular data entity types while excluding other data entity types. Accordingly, these existing systems frequently require users to navigate through a plurality of graphical user interfaces, web pages, and software applications-including, in many instances, running multiple applications in tandem—to access necessary information for determining a therapeutic treatment or for identifying a preclinical model. Consequently, by running and processing the interactions for navigating among various applications, web programs, and applications, such existing systems inefficiently require an excessive amount of time and processing power.

Similarly, conventional systems have similar problems with regard to technical drug discovery pipelines and processes. For example, conventional systems utilize a variety of complex technical processes in the drug discovery pipeline to identify, develop, and test compounds. For example, conventional systems utilize computer implemented techniques for target identification, target validation, hit identification, hit-to-lead optimization, lead optimization, preclinical development, and clinical trials. To illustrate, target identification can include a variety of computer-implemented processes for performing genomic and proteomic analysis, bioinformatics, and disease pathway analysis. For example, conventional systems can perform perturbation assays and utilize computational models to compare results to identify potential gene targets for a therapeutic compound discovery pipeline. These processes are computationally expensive, time-consuming, resource intensive and inefficient. Despite the extensive resources required by these processes they still suffer from significant inaccuracies and inflexibilities as discussed above (e.g., analyzing siloed data sources leading to failed predictions).

In one or more embodiments, the graph modeling system 100 can provide several technological improvements or advantages relative to existing systems. For instance, the graph modeling system 100 can improve flexibility. Specifically, as mentioned above, existing systems rigidly determine therapeutic treatments or identify preclinical models based on sparse amounts of data that is often limited to a particular domain or data entity type. Conversely, the graph modeling system 100 can flexibly determine therapeutic treatments (e.g., a patient stratifications) for one or more patients and/or identify preclinical models that are representative of a patient population from a plurality of data sources and based on data associated with a plurality of data entity types, all within a single, unified framework. For example, the graph modeling system 100 transform signals from a variety of data sources, such as from functional response machine learning embeddings, digital clinical datasets, and/or digital preclinical-model datasets. Further, the graph modeling system 100 can incorporate data associated with a plurality of data types, including data associated with clinical patients, compounds, preclinical models, and/or genes. In the same or other embodiments, the graph modeling system 100 can incorporate data associated additional or alternative data entities, including other biological entities or relationships, such as proteins or signaling pathways.

Additionally, the graph modeling system 100 improves the technological process for determining therapeutic treatments and/or for identifying preclinical models. Specifically, in contrast with conventional approaches that typically operate on isolated data siloes or domains without modeling or leveraging the interconnections between data sources, the graph modeling system 100 can generate and utilize an inclusive, heterogeneous multi-entity graph representation that connects a plurality of data entities corresponding to a plurality of data entity types. Indeed, the graph modeling system 100 can incorporate data obtained from a plurality of data sources, as described above, to generate one or more multi-entity graph representations that include nodes for one or more clinical patients, compounds, preclinical models, genes, and/or biological entities or relationships, such as proteins or signaling pathways. Further, the graph modeling system 100 can connect each of these nodes together with edges, with each edge encoding relationships between each of the nodes. From these one or more multi-entity graph representations, the graph modeling system 100 can utilize a graph neural network such as a graph attention model (e.g., trained on multi-entity graph representation data) to generate embeddings (e.g., node embeddings, edge embeddings, and/or multi-entity graph representation embeddings) within a new latent space, which can be used to intelligently determine the similarity between each of the various data entities. Accordingly, the graph modeling system 100 provides a single, unified process and framework for connecting and determining similarity between the various data entities corresponding to a plurality of data entity types, which can provide for improved overall accuracy, precision, and reliability of therapeutic treatment determinations and preclinical model identification.

Moreover, due at least in part to its improved flexibility and improved technological process, the graph modeling system 100 can improve efficiency. As described above, amongst existing systems that attempt to circumvent their siloed natures, many existing systems utilize software applications or web programs that are rigidly programmed to assess data associated with particular data entity types while excluding other data entity types. As a result, users are often required to navigate through a plurality of graphical user interface, web pages, and applications to access necessary information for determining a therapeutic treatment or for identifying a preclinical model. By contrast, the graph modeling system 100 can provide a single, unified framework and process for accessing or receiving data from a plurality of data sources. Further, this unified approach can also enable incorporation of data associated with a plurality of data entity types to generate one or more multi-entity graph representations, which may be used to connect and assess similarity between diverse data entities. Consequently, the graph modeling system 100 can avoid the inefficiencies of fragmented workflows by eliminating the need for navigating across multiple interfaces or applications, thereby reducing the time and processing power required relative to existing systems.

Further, by utilizing the graph neural network, the graph modeling system 100 is also able to further improve efficiency. To elaborate, the graph modeling system 100 may use the graph neural network in a self-supervised setting to mask edges, edge weights, and/or edge features within a multi-entity graph representation, and prompt (or direct) the graph neural network to predict the edges, weights, and/or features of those masked edges. By employing this self-supervised strategy (e.g., as described in greater detail below in relation to FIG. 6), the graph modeling system 100 may perform various functions-such as determining a therapeutic treatment (e.g., patient stratification) and/or identifying a preclinical mode-without requiring large sets of annotated datapoints, as required in many existing systems.

The graph modeling system 100 further improves technical drug discovery pipelines. Indeed, by generating embeddings from a variety of data sources as just discussed, the graph modeling system 100 can determine flexibly, efficiently, and accurately determine similarities from across various domains to significantly improve drug discovery processes. For example, the graph modeling system 100 can compare embeddings for patients, preclinical models, genes, and/or compounds to determine similarities that inform and short-circuit the drug discovery process. For instance, the graph modeling system 100 can compare embeddings to determine potential targets/hits, initiate programs, analyze potential drug/compound variations, analyze concentration effects and inter-relationships, and determine patient or pre-clinical impacts/relationships of various drugs or genes. Thus, the graph modeling system 100 can significantly improve a variety of stages of the drug discovery pipeline. Indeed, the graph modeling system 100 can lead to more accurate compound predictions with more efficient use of resources from more flexible analysis.

Figure 2:
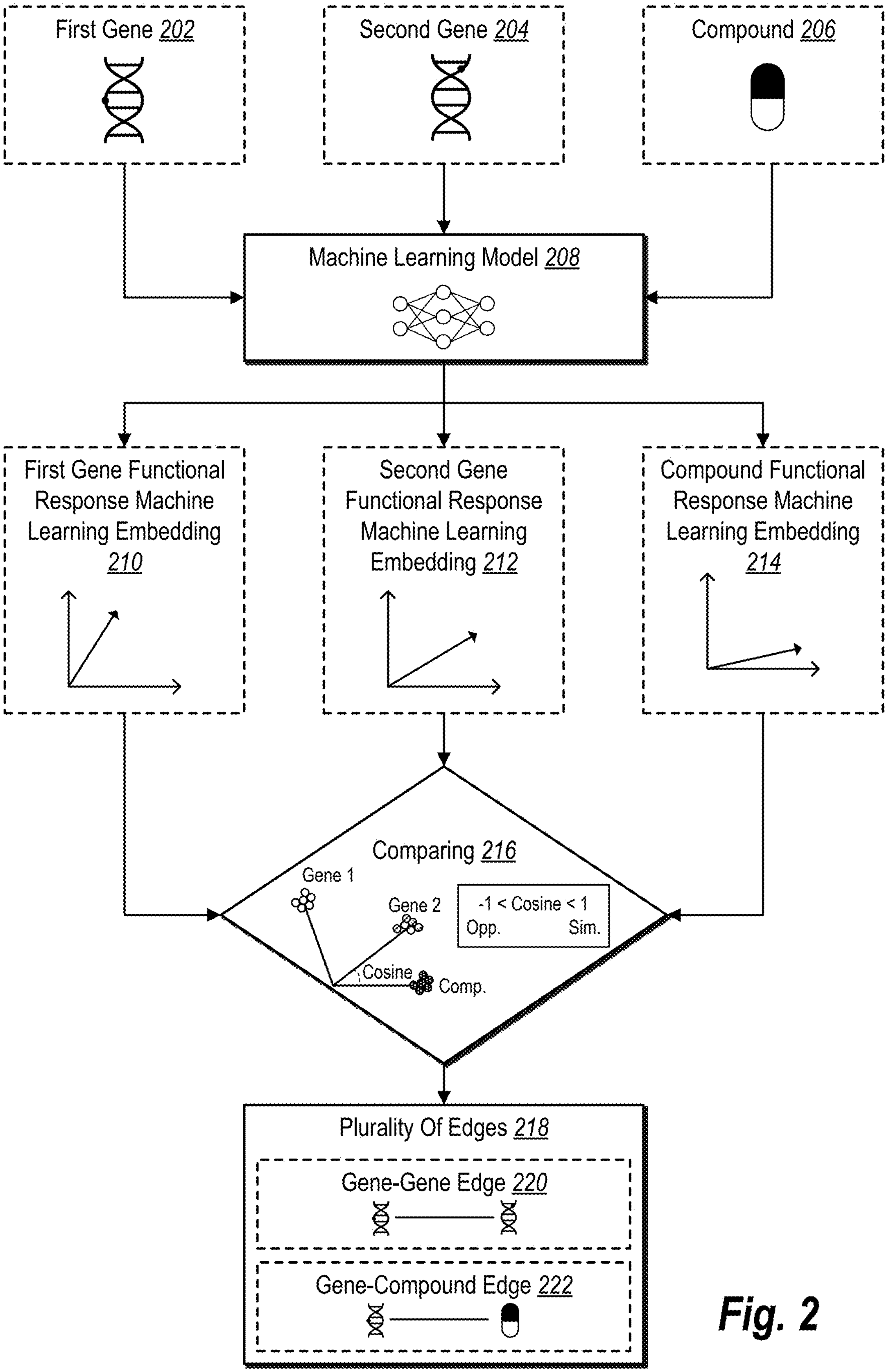
FIG. 2 illustrates an example diagram of a process for generating, from functional response machine learning embeddings, a plurality of edges for a multi-entity graph representation in accordance with one or more embodiments.

As expressed above, the graph modeling system 100 can generate a plurality of edges for a multi-entity graph representation. In particular, the graph modeling system 100 can utilize functional response machine learning embeddings to generate the plurality of edges, including, in some cases, a gene-gene edge and/or a gene-compound edge. FIG. 2 illustrates an example diagram of a process for generating, from functional response machine learning embeddings, a plurality of edges for a multi-entity graph representation in accordance with one or more embodiments.

As illustrated in FIG. 2, the graph modeling system 100 utilizes a machine learning model 208 to generate or identify (e.g., from a functional response embedding store) functional response machine learning embeddings for one or more genes (e.g., a first gene 202 and/or a second gene 204) and/or for one or more compounds (e.g., a compound 206). As used herein, the term "functional response machine learning embedding" refers to a numerical (or vector) representation generated by one or more machine learning models that encode functional response information (e.g., phenomic and/or transcriptomic data embeddings in a continuous, lower-dimensional vector space). For example, a functional response machine learning embedding can include a phenomic embedding (e.g., a perturbation image embedding) derived from one or more images of cells that have undergone a perturbation, such as a genetic perturbation (e.g., a gene knockout, such as a CRISPR knockout, or an RNAi screen) or a chemical compound (e.g., a therapeutic agent). Additionally or alternatively, a functional response machine learning embedding can include a transcriptomic embedding derived from one or more gene expression profiles corresponding to perturbed cellular states. In some instances, a functional response machine learning embedding can represent a phenotypic and/or transcriptional response associated with a perturbation of one or more genes (e.g., one or more target genes).

As used herein, the term "machine learning model" refers to a computer algorithm or a collection of computer algorithms that improve for a particular task through iterative outputs or predictions based on use of data. For example, a machine learning model can utilize one or more learning techniques to improve in accuracy and/or effectiveness. Example machine learning models include various types of decision trees, support vector machines, Bayesian networks, random forest models, or neural networks (e.g., deep neural networks, generative adversarial neural networks, convolutional neural networks, recurrent neural networks, or diffusion neural networks). Similarly, the term "machine learning data" refers to information, data, or files generated or utilized by a machine learning model. Machine learning data can include training data, machine learning parameters, or embeddings/predictions generated by a machine learning model.

As additionally used herein, the term "neural network" refers to a machine learning model that can be trained and/or tuned based on inputs to approximate unknown functions. For example, a neural network includes a model of interconnected artificial neurons (e.g., organized in layers) that communicate and learn to approximate complex functions and generate outputs based on a plurality of inputs provided to the neural network. In some cases, a neural network refers to an algorithm (or a set of algorithms) that implements deep learning techniques to model high-level abstractions in data. A neural network can include various layers such as an input layer, one or more hidden layers, and an output layer that each perform tasks for processing data. For example, a neural network can include a deep neural network a convolutional neural network, a recurrent neural network (e.g., an LSTM), a graph neural network, a large language model, or a generative neural network.

In one or more embodiments, the graph modeling system 100 may utilize the machine learning model 208, implemented as a phenomic machine learning model (e.g., a phenomic neural network), to generate the functional response machine learning embeddings. For instance, the graph modeling system 100 may utilize the phenomic machine learning model to generate phenomic embeddings (e.g., perturbation image embeddings) of one or more cell images. As an example, the graph modeling system 100 utilizes the phenomic machine learning model to synthesize phenomic digital images representing cellular perturbations by embedding the phenomic digital images into a low dimensional space. In some instances, the graph modeling system 100 utilizes a phenomic machine learning model to generate the functional response machine learning embeddings as described in UTILIZING MACHINE LEARNING MODELS TO SYNTHESIZE PERTURBATION DATA TO GENERATE PERTURBATION HEATMAP GRAPHICAL USER INTERFACES, U.S. patent application Ser. No. 18/526,707, filed Dec. 1, 2023, which is incorporated herein by reference in its entirety.

The graph modeling system 100 can also utilize the machine learning model 208, implemented as a generative machine learning model, to generate the functional response machine learning embeddings. In particular, the graph modeling system 100 can train and/or utilize a trained generative machine learning model (e.g., a masked autoencoder generative model and/or a channel-agnostic masked autoencoder generative model) to generate the functional response machine learning embeddings (e.g., perturbation embeddings) from input phenomic microscopy images. In some cases, the graph modeling system 100 utilizes a generative machine learning model to generate the functional response machine learning embeddings as described in UTILIZING MASKED AUTOENCODER GENERATIVE MODELS TO EXTRACT MICROSCOPY REPRESENTATION AUTOENCODER EMBEDDINGS, U.S. patent application Ser. No. 18/545,399, filed Dec. 19, 2023, which is incorporated herein by reference in its entirety. In additional or alternative embodiments, the graph modeling system 100 utilizes a generative machine learning model to generate the functional response machine learning embeddings as described in UTILIZING MASKED AUTOENCODER GENERATIVE MODELS TO EXTRACT CELLULAR RESPONSE REPRESENTATION EMBEDDINGS, U.S. patent application Ser. No. 19/074,095, filed Mar. 7, 2025, which is also incorporated herein by reference in its entirety.

In the same or other embodiments, the graph modeling system 100 can utilize the machine learning model 208, implemented as a transcriptomic machine learning model, to generate the functional response machine learning embeddings. For example, the graph modeling system 100 utilizes the transcriptomic machine learning model (e.g., a transcriptomics foundation model) to generate the functional response machine learning embeddings (e.g., transcriptomic embeddings) corresponding to one or more transcriptomic profiles. The graph modeling system 100 can utilize a variety of different machine learning models or architectures for the transcriptomic machine learning model, including, but not limited to, scVI, Geneformer, scGPT, CellPLM, Universal Cell Embeddings or "UCE," scBERT, and/or scVAEIT. In some embodiments, the graph modeling system 100 utilizes a transcriptomic machine learning model to generate the functional response machine learning embeddings as described in UTILIZING MACHINE LEARNING AND DIGITAL EMBEDDING PROCESSES TO GENERATE DIGITAL MAPS OF BIOLOGY AND USER INTERFACES FOR EVALUATING MAP EFFICACY, U.S. patent application Ser. No. 19/071,348, filed Mar. 5, 2025, which is incorporated herein by reference in its entirety. In additional or alternative embodiments, the graph modeling system 100 utilizes a transcriptomic machine learning model to generate the functional response machine learning embeddings as described in GENERATING TRANSCRIPTOMIC BENCHMARKS FOR TRANSCRIPTOMICS MACHINE LEARNING MODELS UTILIZING A STRUCTURAL INTEGRITY METRIC, U.S. patent application Ser. No. 19/041,384, filed Jan. 30, 2025, which is also incorporated herein by reference in its entirety.

As also illustrated in FIG. 2, the graph modeling system 100 can utilize the machine learning model 208 to generate one or more gene functional response machine learning embeddings and/or one or more compound functional response machine learning embeddings. For instance, the graph modeling system 100 may utilize the machine learning model 208 to generate a first gene functional response machine learning embedding 210 for the first gene 202 from a transcriptomic profile or a phenomic image of a cell exposed to a gene knockout of the first gene 202. Additionally or alternatively, the graph modeling system 100 may utilize the machine learning model 208 to generate a second gene functional response machine learning embedding 212 for the second gene 204 from a transcriptomic profile or a phenomic image of a cell exposed to a gene knockout of the second gene 204. Further, in the same or other embodiments, the graph modeling system 100 may utilize the machine learning model 208 to generate a compound functional response machine learning embedding 214 for the compound 206 from a transcriptomic profile or phenomic image of a cell exposed to the compound 206. Moreover, in at least one embodiment, the graph modeling system 100 may generate an additional compound functional response machine learning embedding for an additional compound from a transcriptomic profile or a phenomic image of a cell exposed to the additional compound.

In one or more embodiments, the graph modeling system 100 may generate nodes for a multi-entity graph representation. For instance, the graph modeling system 100 may generate a first gene node for the first gene 202 and/or a second gene node for the second gene 204, where the first gene node and the second gene node can each include an identifiable vector of features that determines (or identifies) these nodes as a gene nodes. As another example, the graph modeling system 100 may generate a compound node for the compound 206 and/or an additional compound node for the additional compound, where the compound node and the additional compound node can each include an identifiable vector of features that determines (or identifies) these nodes as compound nodes. In some cases, each identifiable vector of features for each of the above nodes may also identify or distinguish characteristics of the specific data entity (e.g., the first gene 202, the second gene 204, the compound 206, and/or the additional compound) associated with each node.

As further illustrated in FIG. 2, the graph modeling system 100 may generate a plurality of edges 218 for the multi-entity graph representation by encoding relationships between the nodes into the edges. In particular, the graph modeling system 100 may generate the plurality of edges 218 by performing the act 216 of comparing at least two of the functional response machine learning embeddings. For example, the graph modeling system 100 may generate a gene-gene edge 220 between the first gene node and the second gene node by comparing the first gene functional response machine learning embedding 210 and the second gene functional response machine learning embedding 212. Additionally or alternatively, the graph modeling system 100 may generate a gene-compound edge 222 between the first gene node (or the second gene node) and the compound node (or the additional compound node) by comparing the first gene functional response machine learning embedding 210 (or the second gene functional response machine learning embedding 212) and the compound functional response machine learning embedding 214 (or the additional compound functional response machine learning embedding). Further, in the same or other embodiments, the graph modeling system 100 may generate a compound-compound edge between the compound node and the additional compound node by comparing the compound functional response machine learning embedding 214 and the additional compound functional response machine learning embedding.

In one or more embodiments, the graph modeling system 100 may perform the act 216 to generate the plurality of edges 218 based on determining a similarity measure between at least two functional response machine learning embeddings. For instance, the graph modeling system 100 can generate the plurality of edges based on cosine similarity or another feature space distance measurement (e.g., Euclidean distance between feature vectors) between the at least two functional response machine learning embeddings. As an example, the graph modeling system 100 may generate the gene-gene edge 220 based on determining a cosine similarity between the first gene functional response machine learning embedding 210 and the second gene functional response machine learning embedding 212. As another example, the graph modeling system 100 may generate the gene-compound edge 222 based on determining a cosine similarity between the first gene functional response machine learning embedding 210 and the compound functional response machine learning embedding 214. As yet another example, the graph modeling system 100 may generate the compound-compound edge based on determining a cosine similarity between the compound functional response machine learning embedding 214 and the additional compound functional response machine learning embedding.

In one or more embodiments, the graph modeling system 100 assigns edge weights to the plurality of edges 218 based on the act 216. For instance, the graph modeling system 100 may assign an edge weight to the gene-gene edge 220, the gene-compound edge 222, and/or the compound-compound edge. Indeed, the graph modeling system 100 may assign the edge weights to reflect the degree of similarity or relatedness between corresponding nodes, where higher weights indicate stronger similarity.

Figure 3:
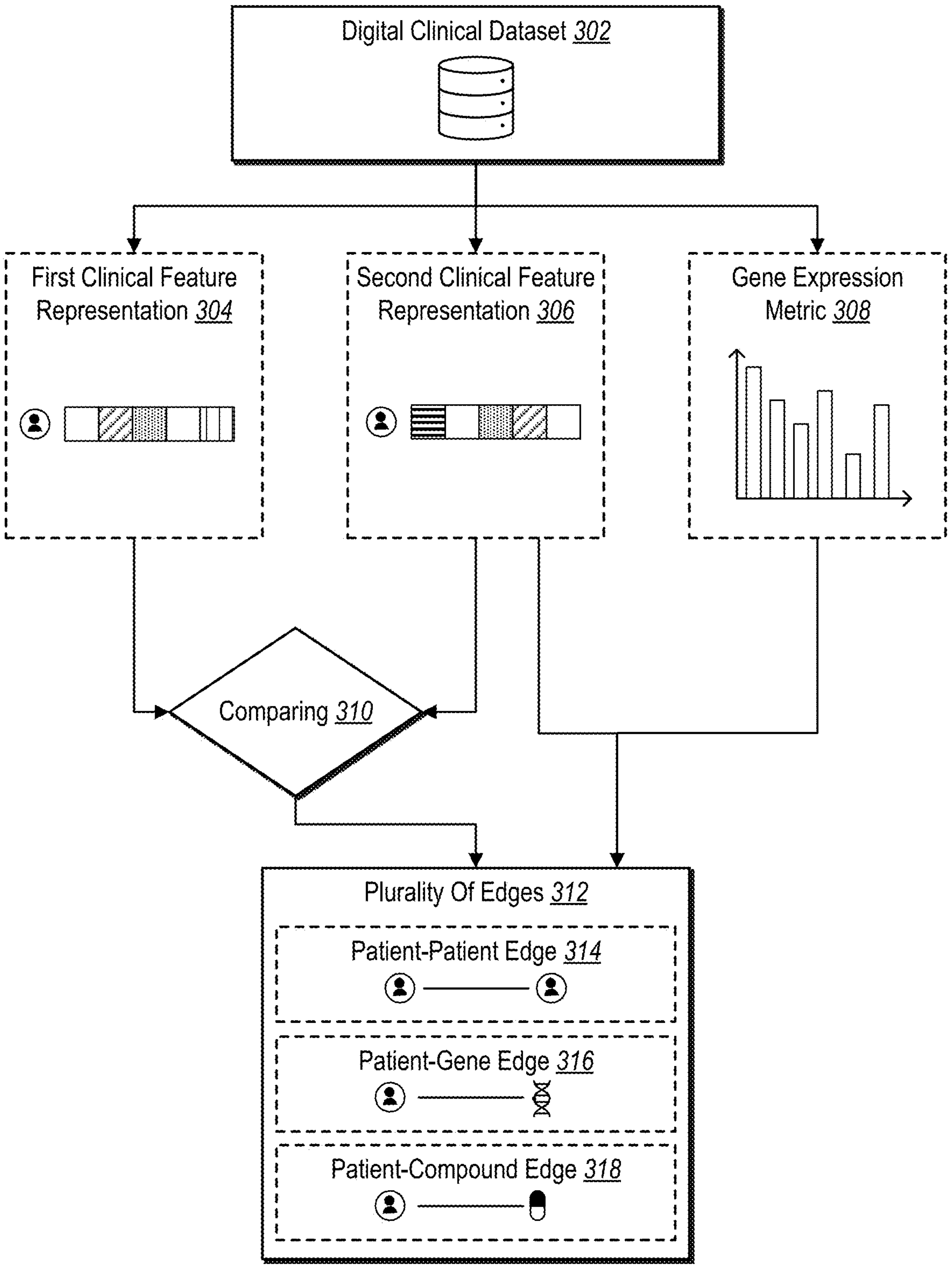
FIG. 3 illustrates an example diagram of a process for generating, utilizing a digital clinical dataset, a plurality of edges for a multi-entity graph representation in accordance with one or more embodiments.

As expressed above, the graph modeling system 100 can generate a plurality of edges for a multi-entity graph representation. In particular, the graph modeling system 100 can utilize a digital clinical dataset to generate the plurality of edges, which can include, in some cases, a patient-patient edge and/or a patient-gene edge. FIG. 3 illustrates an example diagram of a process for generating, utilizing a digital clinical dataset, a plurality of edges for a multi-entity graph representation in accordance with one or more embodiments.

As illustrated in FIG. 3, the graph modeling system 100 accesses or receives data associated with a plurality of clinical patients (e.g., having one or more diseases such as cancer) from a digital clinical dataset 302. As used herein, the term "digital clinical dataset" refers to a collection of clinical, genetic, and/or phenotypic data stored in a structured digital format and associated with a plurality of clinical patients (e.g., having a disease). In particular, a digital clinical dataset can include data obtained from internal sources and/or external or third-party sources (e.g., public datasets, commercial providers, research collaborations, and/or data repositories). For example, a digital clinical dataset can include clinical records and/or patient-specific data encompassing patient genetic data, clinical variables data, and/or clinical outcomes data.

In one or more embodiments, the graph modeling system 100 accesses or receives data from the digital clinical dataset 302 that includes, for example, patient genetic data, clinical variables data, and/or clinical outcomes data. For instance, the patient genetic data can include DNA data and/or RNA data corresponding to the plurality of clinical patients. To elaborate, DNA data can include genomic sequences, structural variations, mutation profiles, and/or other indicators of genomic content obtained through assays such as whole-genome sequencing, whole-exome sequencing, or targeted panel sequencing. For example, DNA data can include single-nucleotide polymorphisms (SNPs), insertions or deletions (indels), copy number variations (CNVs), methylation states, chromosomal aberrations, and/or variant call data for a plurality of genes or loci. Further, RNA data can include transcriptomic measurements that reflect the abundance, structure, and/or sequence of RNA molecules expressed within a cell or tissue sample. For example, RNA data can include gene expression levels, transcript isoform counts, splicing patterns, non-coding RNA profiles, and/or other transcriptomic features obtained from bulk or single-cell RNA sequencing, microarrays, or related technologies. Further, in at least one embodiment, the patient genetic data may include processed or normalized representations of the DNA data and/or the RNA data, such as variant call formats (VCFs), gene-level expression matrices, and/or transcript abundance scores (e.g., to indicate expression levels of specific RNA transcripts).

As mentioned above, the digital clinical dataset 302 can include clinical variables data. To elaborate, clinical variables data can include a collection of patient-specific values associated with one or more clinical variables stored in a structured format for use in computational analysis. In some cases, a clinical variable can refer to any measurable or categorical clinical attribute of a clinical patient. For example, a clinical variable may reflect demographic characteristics (e.g., age, sex, race/ethnicity), disease characteristics (e.g., diagnosis, tumor type, biomarker status, onset data), clinical history and comorbidity indicators (e.g., prior or concurrent diagnoses, smoking and alcohol use status, family history of the disease), treatment history (e.g., medications or compounds used in treatment), physiological status, and/or laboratory and diagnostic results (e.g., histology).

As also mentioned above, the digital clinical dataset 302 can include clinical outcomes data. In particular, clinical outcomes data can include structured information reflecting health status, disease progression, treatment response, and/or overall clinical trajectories of a patient and/or disease over time. For example, clinical outcomes data may include one or more outcome variables that represent survival, therapeutic efficacy, recurrence, and/or other patient-level endpoints relevant to clinical evaluation. In some embodiments, clinical outcomes data may include binary clinical outcomes data and/or non-binary clinical outcomes data.

As also illustrated in FIG. 3, the graph modeling system 100 can generate one or more clinical feature representations for clinical patients. As used herein, the term "clinical feature representation" refers to a data structure or vector that encodes one or more features associated with a clinical patient. In particular, a clinical feature representation can be generated for one or more clinical patients based on data accessed or received from a digital clinical dataset. For example, a clinical feature representation can include a representation for a particular clinical patient based on patient genetic data, clinical variables data, and/or clinical outcomes data.

For instance, the graph modeling system 100 can generate a first clinical feature representation 304 for a first clinical patient. In particular, the graph modeling system 100 can identify features associated with the first clinical patient from the data (e.g., patient genetic data, clinical variables data, and/or clinical outcomes data) accessed or received from the digital clinical dataset 302. Upon identifying these features, the graph modeling system 100 may generate a first data structure or a first vector that encodes the features associated with the first clinical patient.

Additionally or alternatively, the graph modeling system 100 can generate a second clinical feature representation 306 for a second clinical patient. Specifically, the graph modeling system 100 can identify features associated with the second clinical patient from the data (e.g., patient genetic data, clinical variables data, and/or clinical outcomes data) accessed or received from the digital clinical dataset 302. Upon identifying these features, the graph modeling system 100 may generate a second data structure or a second vector that encodes the features associated with the second clinical patient.

As further illustrated in FIG. 3, the graph modeling system 100 can identify (or determine) gene expression metrics for clinical patients with respect to particular genes. As used herein, the term "gene expression metric" refers to a data value or data structure that characterizes the level or status of expression of a gene within a biological sample. In particular, a gene expression metric can represent the expression of a gene in a clinical patient or a preclinical model based on DNA data and/or RNA data accessed or received from a digital clinical dataset or a digital preclinical-model dataset. For example, a gene expression metric can include a normalized scalar expression value, a categorical or binary status (e.g., overexpressed or underexpressed), a binarized presence/absence status for a particular gene in a given sample, and/or a graphical or structured representation (e.g., a vector or matrix encoding expression values across time points, tissues, and/or conditions). In some embodiments, a gene expression metric for a preclinical model can be determined based on transcriptomic or phenotypic response data generated by exposing the preclinical model (e.g., a cell line, organoid, or xenograft) to a genetic or chemical compound perturbation, such as a gene knockout or compound treatment.

For example, the graph modeling system 100 may identify (or determine) a gene expression metric 308 for, for example, the second clinical patient with respect to a gene. Specifically, the graph modeling system 100 may identify the gene expression metric 308 for the second clinical patient from DNA data and/or RNA data accessed or received from the digital clinical dataset 302. As another example, the graph modeling system 100 may identify (or determine) an additional gene expression metric for the first clinical patient with respect to an additional gene (e.g., by following the process just described in relation to the gene expression metric 308).

In one or more embodiments, the graph modeling system 100 may generate nodes for a multi-entity graph representation. For instance, the graph modeling system 100 may generate a first patient node for the first clinical patient and/or a second patient node for the second clinical patient, where the first patient node and the second patient node can each include an identifiable vector of features that determines (or identifies) these nodes as patient nodes. As another example, the graph modeling system 100 may generate a gene node for the gene associated with the second clinical patent and/or an additional gene node for the additional gene associated with the first clinical patient. In some cases, the gene node and the additional gene node can each include an identifiable vector of features that determines (or identifies) these nodes as gene nodes. Further, the graph modeling system 100 may generate one or more compound nodes for one or more compounds associated with one or more clinical patients (e.g., a first edge between a first clinical patient and a first compound a second edge between a second clinical patient and a second compound). In some cases, each identifiable vector of features for each of the above nodes may also identify or distinguish characteristics of the specific data entity (e.g., the first clinical patient, the second clinical patient, the gene, and/or the additional gene) associated with each node.

Additionally, as illustrated in FIG. 3, the graph modeling system 100 may generate a plurality of edges 312 for the multi-entity graph representation by encoding relationships between the nodes into the edges. In some instances, the graph modeling system 100 generates the plurality of edges 312 by performing the act 310 of comparing at least two clinical feature representations. For example, the graph modeling system 100 may generate a patient-patient edge 314 between the first patient node and the second patient node by comparing the first clinical feature representation 304 and the second clinical feature representation 306.

To elaborate, the graph modeling system 100 can generate the patient-patient edge 314 based on determining a similarity measure between the first clinical feature representation 304 and the second clinical feature representation 306. For instance, the graph modeling system 100 can determine a distance between the first clinical feature representation 304 and the second clinical feature representation 306 using a distance-based similarity metric, such as Gower distance. As an example, the graph modeling system 100 may use Gower distance to compute a similarity measure between the first clinical feature representation 304 and the second clinical feature representation 306 by calculating feature-wise dissimilarities (or feature-wise similarities) across features (e.g., of mixed data types, such as numerical, categorical, ordinal, and/or binary variables) of both clinical feature representations, normalizing those dissimilarities (or similarities) to a common scale, and aggregating the results into a single composite distance score. Further, the graph modeling system 100 may assign an edge weight to the patient-patient edge that may reflect the degree of similarity distance between the first patient node and the second patient node, where a higher weight can indicate stronger similarity between the first patient node and the second patient node.

In the same or other embodiments, the graph modeling system 100 additionally or alternatively generates a patient-gene edge 316 between the gene node (or the additional gene node) and a patient node (e.g., the first patient node or the second patient node). For instance, the graph modeling system 100 can generate the patient-gene edge 316 based on the gene expression metric 308. As an example, the system can use normalized gene expression values to quantify the level of expression of the gene in the patient's biological sample. The graph modeling system 100 may then use this expression value to determine whether to form an edge between the patient node and the gene node (e.g., if the expression value is above a particular threshold value). The graph modeling system 100 may also assign an edge weight to reflect the expression level, where a higher normalized expression value may result in a stronger edge weight (which can indicate greater transcriptional activity of the gene in the given patient).

Additionally or alternatively, the graph modeling system 100 may generate a gene-gene edge between the gene node and the additional gene node. To elaborate, the graph modeling system 100 may generate the gene-gene edge by comparing the gene expression metric 308 and the additional gene expression metric. Specifically, the graph modeling system 100 may determine a similarity or correlation measure between the two gene expression metrics to assess the degree of co-expression or transcriptional association between the corresponding genes. For instance, the graph modeling system 100 may compute a Pearson correlation coefficient, cosine similarity, or other statistical measure based on expression values across one or more clinical patients. In some embodiments, graph modeling system 100 may generate the gene-gene edge if a correlation (or similarity) exceeds a predefined threshold. The graph modeling system 100 may also assign an edge weight to reflect the degree of similarity or relatedness between the two nodes, where higher weights indicate stronger similarity.

In some implementations, the graph modeling system 100 generates a gene-gene edge based on the gene expression metrics as described in FIG. 3 and comparing gene functional response machine learning embeddings as described in FIG. 2. For example, the graph modeling system 100 can determine a first similarity based on gene expression metrics of digital clinical datasets and a second similarity based on functional response machine learning embeddings. The graph modeling system 100 can combine the first similarity and second similarity (e.g., add, average, multiply, etc.) to generate the gene-gene edge between the two underlying genes. The graph modeling system 100 can also generate a gene-gene edge based on gene expression metrics from more than two sources (e.g., the gene expression metrics described in relation to FIG. 4). Moreover, the graph modeling system 100 can also combine multiple similarity metrics for gene-compound edges (e.g., gene compound similarity metrics as described in FIG. 2 and similarities determine by comparing compound-gene expression metrics of FIG. 4).

Further, the graph modeling system 100 may generate a patient-compound edge 318 between a patient node and a compound node. For example, the graph modeling system 100 can connect a patient node corresponding to a clinical patient who has received a therapy to a compound node corresponding to a first-line compound (e.g., the compound used to treat the clinical patient in the therapy) based on a response derived from longitudinal data. In some embodiments, the graph modeling system 100 may additionally or alternatively generate a compound-compound node. As an example, the graph modeling system 100 may connect an additional compound node corresponding to a new compound (e.g., a newly discovered compound) to the compound node corresponding to the first-line compound based on, for instance, a genetic effect relationship (e.g., a shared genetic effect) and/or chemical structure similarity. Moreover, the graph modeling system 100 may generate a gene-compound edge between the additional compound node to a gene node corresponding to a relevant gene(s), which may be associated with clinical patient profiles or other compounds. In this way, compounds can not only be utilized in a preclinical context (e.g., with preclinical models, as described in greater detail below in relation to FIG. 4) but also a clinical context.

Figure 4:
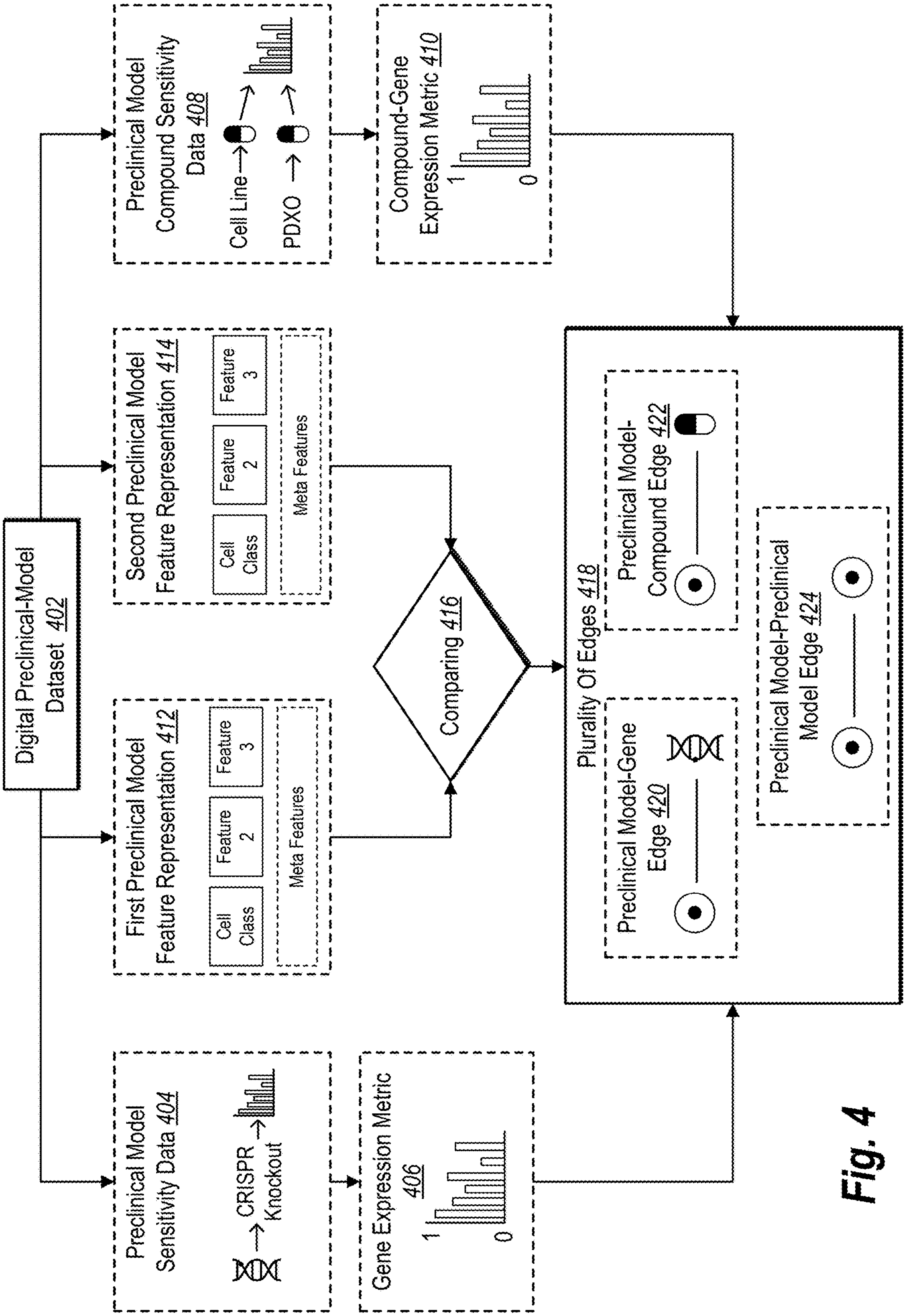
FIG. 4 illustrates an example diagram of a process for generating, utilizing a digital preclinical-model dataset, a plurality of edges for a multi-entity graph representation in accordance with one or more embodiments.

As expressed above, the graph modeling system 100 can generate a plurality of edges for a multi-entity graph representation. In particular, the graph modeling system 100 can utilize a digital preclinical-model dataset to generate the plurality of edges, which can include, in some cases, a preclinical model-gene edge, a preclinical model-compound edge, and/or a preclinical model-preclinical model edge. FIG. 4 illustrates an example diagram of a process for generating, utilizing a digital preclinical-model dataset, a plurality of edges for a multi-entity graph representation in accordance with one or more embodiments.

As illustrated in FIG. 4, the graph modeling system 100 accesses or receives data associated with one or more preclinical models from a digital preclinical-model dataset 402. As used herein, the term "digital preclinical-model dataset" refers to a collection of structured digital data associated with one or more preclinical models. In particular, a digital preclinical-model dataset can include molecular, phenotypic, and/or experimental response data derived from in vitro or in vivo biological models used in research and development settings. For example, a digital preclinical-model dataset can include data associated with preclinical models such as cancer cell lines, organoids (e.g., patient-derived organoids or PDOs), patient-derived xenografts (PDXs), patient-derived xenograft organoids (PDXOs), and/or animal models. Further, a digital preclinical-model dataset may contain preclinical model sensitivity data, as well as additional molecular or phenotypic data (e.g., baseline gene expression profiles, protein expression data, imaging-derived phenotypic features) and/or metadata describing model characteristics such as tissue of origin, mutation status, or molecular subtype.

As also described herein, the term "preclinical model sensitivity data" refers to data that characterizes how a preclinical model responds to a biological or chemical compound perturbation. In particular, preclinical model sensitivity data can represent the degree or nature of a response exhibited by a preclinical model such as a cell line, xenograft (e.g., a PDX), organoid (e.g., a PDO or PDXO), or other preclinical model when exposed to a perturbation, such as a genetic perturbation (e.g., a gene knockout, such as a CRISPR knockout, or an RNAi screen) or a chemical compound (e.g., a therapeutic agent). perturbation response profiles such as gene expression data measured following perturbation, viability scores, proliferation rates, transcriptomic changes, phenotypic measurements (e.g., image-derived features), or dose-response metrics (e.g., $IC_{50}$, AUC), obtained from a cell line or xenograft subjected to CRISPR-based gene knockout or compound treatment. In some cases, the term "preclinical model compound sensitivity data" can, in some cases, be used to more particularly refer to preclinical model sensitivity data that represents the degree or nature of a response exhibited by a preclinical model when exposed to a chemical compound perturbation.

As also illustrated in FIG. 4, the graph modeling system 100 can identify (or determine) gene expression metrics of preclinical models exposed to perturbations. For instance, the graph modeling system 100 can access or receive, from the digital preclinical-model dataset 402, preclinical model sensitivity data 404 associated with one or more preclinical models (e.g., a cell line or a xenograft). From the preclinical model sensitivity data 404, the graph modeling system 100 may identify a gene expression metric 406 of a preclinical model exposed to a genetic perturbation (e.g., a gene knockout, such as a CRISPR knockout, or an RNAi screen).

Additionally or alternatively, as illustrated in FIG. 4, the graph modeling system 100 may identify (or determine) a compound-gene expression metric 410. As used herein, a "compound-gene expression metric" refers to a gene expression metric identified (or determined) from sensitivity data associated with chemical compound perturbation, such as from preclinical model compound sensitivity data. To elaborate, the graph modeling system 100 may access or receive, from the digital preclinical-model dataset 402, preclinical model compound sensitivity data 408 associated with one or more preclinical models (e.g., a cell line or a xenograft). From the preclinical model compound sensitivity data 408, the graph modeling system 100 may identify a compound-gene expression metric 410 of a preclinical model exposed to a chemical compound perturbation.

As further illustrated in FIG. 4, the graph modeling system 100 may generate one or more preclinical model feature representations for preclinical models. As used herein, the term "preclinical model feature representation" refers to a data structure or vector that encodes one or more features associated with a preclinical model. In particular, a preclinical model feature representation can be generated for one or more preclinical models based on data accessed or received from a digital preclinical-model dataset. For example, a preclinical model feature representation can include a representation for a particular preclinical model (e.g., a cell line, xenograft, or organoid) based on perturbation response data, transcriptomic or phenotypic measurements, and/or meta features, such as tissue of origin, mutation status, molecular subtype, or model type.

For instance, the graph modeling system 100 can generate a first preclinical model feature representation 412 for a first preclinical model. In particular, the graph modeling system 100 can identify features (e.g., a cell class) and/or meta features associated with the first preclinical model from the data accessed or received from the digital preclinical-model dataset 402. Upon identifying these features and/or meta features, the graph modeling system 100 may generate a first data structure or a first vector that encodes the features and/or meta features associated with the first preclinical model.

Additionally or alternatively, the graph modeling system 100 can generate a second preclinical model feature representation 414 for a second preclinical model. Specifically, the graph modeling system 100 can identify features (e.g., a cell class) and/or meta features associated with the second preclinical model from the data accessed or received from the digital preclinical-model dataset 402. Upon identifying these features and/or meta features, the graph modeling system 100 may generate a second data structure or a second vector that encodes the features and/or meta features associated with the second preclinical model.

In one or more embodiments, the graph modeling system 100 may generate nodes for a multi-entity graph representation. For instance, the graph modeling system 100 may generate a first preclinical model node for the first preclinical model and/or a second preclinical model node for the second preclinical model, where the first preclinical model node and the second preclinical model node can each include an identifiable vector of features that determines (or identifies) these nodes as preclinical model nodes. As another example, the graph modeling system 100 may generate a gene node for the gene associated with the preclinical model exposed to the genetic perturbation and/or a compound node for the compound associated with the preclinical model exposed to the chemical compound perturbation. In some cases, the gene node and the compound node can each include an identifiable vector of features that determines (or identifies) these nodes as a gene node or as a compound node, respectively. In some cases, each identifiable vector of features for each of the above nodes may also identify or distinguish characteristics of the specific data entity (e.g., the first preclinical model, the second preclinical model, the gene, and/or the compound) associated with each node.

As shown in FIG. 4, the graph modeling system 100 may generate a plurality of edges 418 for the multi-entity graph representation by encoding relationships between the nodes into the edges. In some embodiments, the graph modeling system 100 may generate a preclinical model-gene edge 420 between a preclinical model node (e.g., the first preclinical model node or the second preclinical model node) and the gene node. For instance, the graph modeling system 100 can generate the preclinical model-gene edge 420 based on the gene expression metric 406. As an example, the system can use normalized gene expression values to quantify the level of expression of the gene in the preclinical model. The graph modeling system 100 may then use this expression value to determine whether to form an edge between the preclinical model node and the gene node (e.g., if the expression value is above a particular threshold value). The graph modeling system 100 may also assign an edge weight to reflect the expression level, where a higher normalized expression value may result in a stronger edge weight.

Additionally or alternatively, the graph modeling system 100 may generate a preclinical model-compound edge 422 between a preclinical model node (e.g., the first preclinical model node or the second preclinical model node) and the compound node. For instance, the graph modeling system 100 can generate the preclinical model-compound edge 422 based on the compound-gene expression metric 410. As an example, the graph modeling system 100 can use normalized compound-gene expression values to quantify the transcriptional response of a gene in the preclinical model following exposure to the compound. The graph modeling system 100 may use this expression value to determine whether to form an edge between the preclinical model node and the compound node (e.g., if the gene's expression change following exposure to the compound exceeds a predefined threshold indicating a significant response). The graph modeling system 100 may also assign an edge weight to reflect the magnitude or direction of the transcriptional effect, such that a stronger or more biologically relevant expression change results in a higher edge weight.

In the same or other embodiments, the graph modeling system 100 generates the plurality of edges 418 by performing the act 416 of comparing at least two preclinical model feature representations. For example, the graph modeling system 100 may generate a preclinical model-preclinical model edge 424 between the first preclinical model node and the second preclinical model node by comparing the first preclinical model feature representation 412 and the second preclinical model feature representation 414.

To elaborate, the graph modeling system 100 can generate the preclinical model-preclinical model edge 424 based on determining a similarity measure between the first preclinical model feature representation 412 and the second preclinical model feature representation 414. For instance, the graph modeling system 100 can determine a similarity score or distance metric between the two feature representations using information encoded in features and/or meta features. As an example, the graph modeling system 100 may derive (or compute) a similarity measure between the first preclinical model feature representation 412 and the second preclinical model feature representation 414 by comparing features and/or meta features associated with each model. To illustrate, the graph modeling system 100 may compare meta features such as small cell lung cancer (SCLC) subtype defined by NAPY classification, where NAPY can refer to the four transcription factors: NEUROD1, ASCL1, POU2F3, and YAP1. Additionally or alternatively, the graph modeling system 100 may derive a similarity measure based on expression profiles of each preclinical model, how each preclinical model responds to one or more compounds, and/or other characteristics data, including metadata of each preclinical model (e.g., to determine that both preclinical models are from the same patient population, have the same cancer type and/or subtype, etc.).

In one or more embodiments, the graph modeling system 100 may use a distance-based similarity metric such as Gower distance to evaluate feature-wise dissimilarities (or similarities) across numerical, categorical, ordinal, and/or binary variables in the preclinical model feature representations, normalize those values to a common scale, and aggregate the results into a single composite similarity or distance score. Further, the graph modeling system 100 may assign an edge weight to the preclinical model-preclinical model edge 424 based on the resulting similarity score, where a higher weight may indicate stronger similarity between the first preclinical model node and the second preclinical model node.

In one or more embodiments, the graph modeling system 100 may also generate one or more additional or alternative edges for the plurality of edges 418. For instance, the graph modeling system 100 may generate a gene-gene edge, a gene-compound edge, and/or a compound-compound edge. For example, the graph modeling system 100 may generate the gene-gene edge by comparing the gene expression metric 406 and an additional gene expression metric corresponding to an additional gene. Additionally or alternatively, the graph modeling system 100 may generate the gene-compound edge by comparing the gene expression metric 406 and the compound-gene expression metric 410. Further, in the same or other embodiments, the graph modeling system 100 may generate the compound-compound edge by comparing the compound-gene expression metric 410 and an additional compound-gene expression metric corresponding to an additional compound.

Specifically, for the gene-gene edge, the gene-compound edge, and/or the compound-compound edge, the graph modeling system 100 may determine a similarity or correlation measure between the expression metrics to assess the degree of co-expression or transcriptional association between the corresponding genes and/or compounds. For instance, the graph modeling system 100 may compute a Pearson correlation coefficient, cosine similarity, or other statistical measure based on expression values across one or more clinical patients. In some embodiments, graph modeling system 100 may generate the gene-gene edge, the gene-compound edge, and/or the compound-compound edge if a correlation (or similarity) exceeds a predefined threshold. As mentioned above, the graph modeling system 100 can also generate gene-gene edges, gene-compound edges, and/or compound-compound edges by comparing functional response machine learning embeddings. The graph modeling system 100 may also assign an edge weight to one or more of these edges to reflect the degree of similarity or relatedness between the two nodes, where higher weights indicate stronger similarity.

Figure 5:
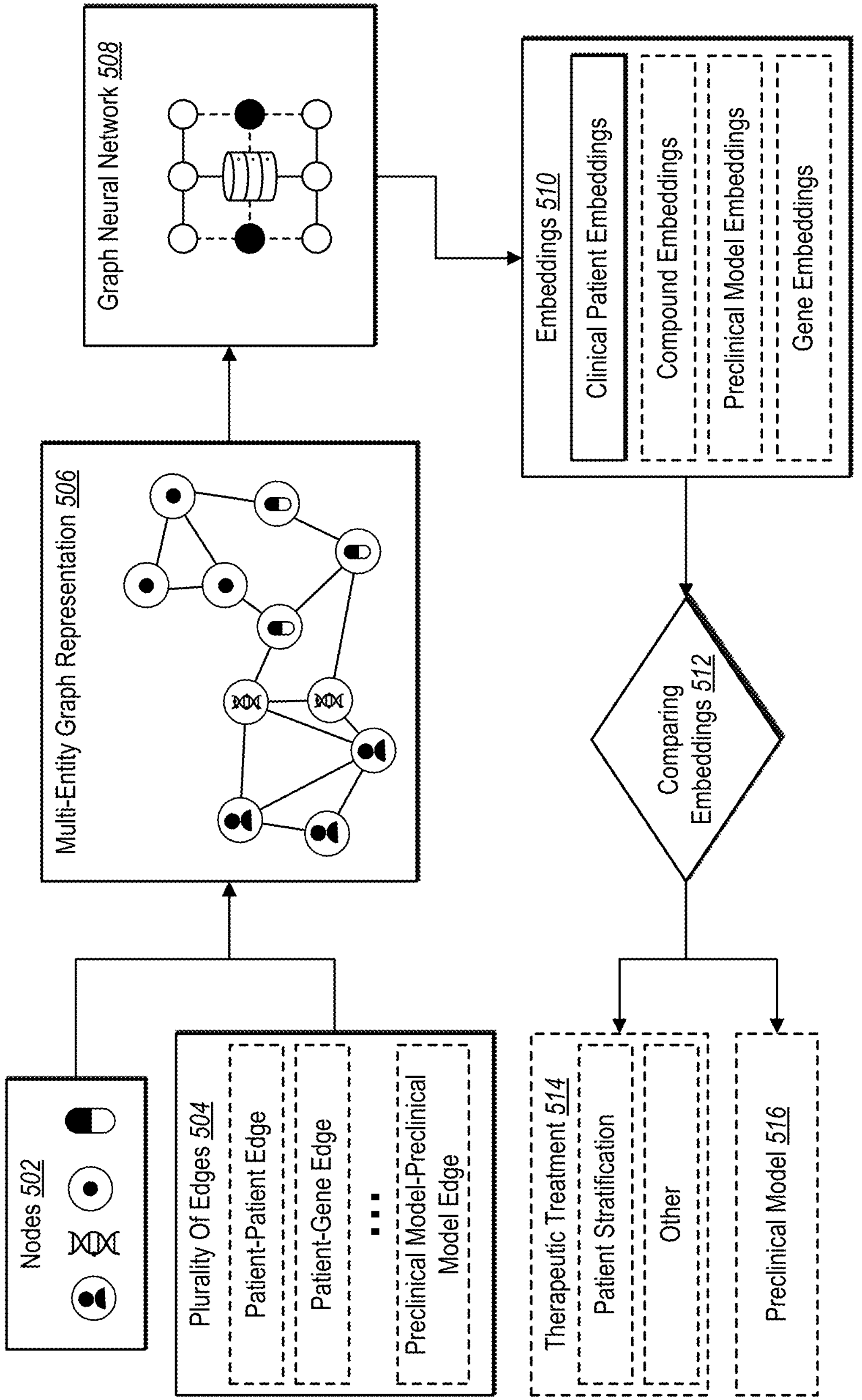
FIG. 5 illustrates an example diagram of a process for determining a therapeutic treatment and/or identifying a preclinical model utilizing a multi-entity graph representation and a graph neural network in accordance with one or more embodiments.

As expressed above, the graph modeling system 100 can determine a therapeutic treatment for one or more patients and/or identify a preclinical model representative of a patient population. Specifically, the graph modeling system 100 may generate and utilize a multi-entity graph representation and a graph neural network to determine the therapeutic treatment and/or to identify the preclinical model. FIG. 5 illustrates an example diagram of a process for determining a therapeutic treatment and/or identifying a preclinical model utilizing a multi-entity graph representation and a graph neural network in accordance with one or more embodiments.

As illustrated in FIG. 5, the graph modeling system 100 generates nodes 502 for a plurality of data entities. In particular, the graph modeling system 100 generates the nodes 502 for a plurality of data entities that may include a clinical patient, a compound, a preclinical model, and/or a gene. For instance, the graph modeling system 100 may generate a patient node corresponding to a particular clinical patient, a compound node corresponding to a particular compound, a preclinical model node corresponding to a particular preclinical model, and/or a gene node corresponding to a particular gene. In the same or other embodiments, the graph modeling system 100 generates the nodes 502 for additional or alternative data entities of the plurality of data entities, including for other biological entities or relationships, such as proteins or signaling pathways. Thus, for instance, the graph modeling system 100 may generate a protein node and/or a signaling pathway node. In some embodiments, the graph modeling system 100 generates the nodes as described above in relation to FIGS. 2-4.

In at least one embodiment, the graph modeling system 100 generates a first plurality of nodes that may include patient nodes for a plurality of clinical patients. Further, the graph modeling system 100 may generate a second plurality of nodes that may include at least one of compound nodes, preclinical model nodes, or gene nodes. In addition, the graph modeling system 100 may generate a third and/or fourth plurality of nodes that may also include at least one of compound nodes, preclinical model nodes, or gene nodes. In some instances, the graph modeling system 100 may generate other node types in addition to the patient nodes, compound nodes, preclinical model nodes, and/or gene nodes.

As also illustrated in FIG. 5, the graph modeling system 100 generates a plurality of edges 504 between at least two of the nodes 502. Specifically, the graph modeling system 100 may generate the plurality of edges 504 that may include a gene-gene edge between two gene nodes, a gene-compound edge between a gene node and a compound node, a compound-compound edge between two compound nodes, a patient-patient edge between two patient nodes, a patient-gene edge between a patient node and a gene node, a patient-compound edge between a patient node and a compound node, a preclinical model-gene edge between a preclinical model node and a gene node, a preclinical model-compound edge between a preclinical model node and a compound node, and/or preclinical model-preclinical model edge between two preclinical model nodes. Additionally or alternatively, the plurality of edges 504 may include edges that connect a protein node, signaling pathway node, and/or other biological entity or relationship node to another node of the nodes 502 (e.g., a protein-protein edge, clinical patient-protein edge, and/or a gene-protein edge). In some cases, the plurality of edges 504 encode relationships between the nodes into the edges. For example, each edge may include a continuous score (e.g., quantifying the strength, similarity, or relationship between two nodes) and/or a genetic score for determining similarity between two nodes.

Further, each edge in the plurality of edges 504 may include an identifiable vector comprising one or more features that determine, identify, specify, or otherwise encode identity characteristics of each edge, such as an edge type—that is, the type of relationship represented by each edge (e.g., patient-patient, gene-gene, etc.). Additionally or alternatively, each edge may include one or more edge weights that quantify the strength, similarity, or relevance of the relationship between the corresponding nodes. In some cases, the edge weight may be derived from a similarity score, correlation coefficient, distance metric, or response magnitude, and may be used during downstream graph processing to influence traversal, embedding generation, or treatment inference. Indeed, the graph modeling system 100 may generate a weight for an edge if, for example, a similarity score, correlation coefficient, distance metric, or response magnitude is above a predefined threshold. In at least one embodiment, the graph modeling system 100 generates the plurality of edges 504 as described above in relation to FIGS. 2-4.

As mentioned above, in some implementations, the graph modeling system 100 generates edge weights so that they are comparable across different relationships between nodes. For example, in some embodiments, the graph modeling system 100 normalizes the edge weights (e.g., between 0 and 1, −1 to 1, 0 to 100, or −100 to 100). In some embodiments, the graph modeling system 100 utilizes statistical measures (e.g., mean and standard deviation) to normalize edge weights between common nodes based on common features. Thus, for example, the graph modeling system 100 normalizes all patient-patient edges utilizing statistical measures of all patient-patient edges and normalizes all pre-clinical model-pre-clinical model edges utilizing statistical measures of all pre-clinical model-pre-clinical model edges.

Additionally, as illustrated in FIG. 5, the graph modeling system 100 generates a multi-entity graph representation 506 corresponding to the plurality of data entities. As used herein, the term "multi-entity graph representation" refers to a data structure that models a set of entities and the relationships between them using nodes and edges. In particular, a multi-entity graph representation can be generated based on (or to include) nodes (e.g., one or more pluralities of nodes) corresponding to distinct entity types and a plurality of edges representing relationships, similarities, or interactions among those entities. For example, a multi-entity graph representation may include nodes representing clinical patients, genes, compounds, and/or preclinical models, and edges representing similarity scores, perturbation effects, co-expression relationships, or treatment response associations between these entities.

To elaborate, the graph modeling system 100 may generate the multi-entity graph representation 506 based on (or to include) the nodes 502 and the plurality of edges 504. Indeed, the graph modeling system 100 may generate the multi-entity graph representation 506 to include one or more nodes of the nodes 502 interconnected together by the plurality of edges 504 all within a single graph representation. As an example, the graph modeling system 100 may generate the multi-entity graph representation 506 based on, or that includes, the first plurality of nodes for the plurality of clinical patients connected to (e.g., via the plurality of edges 504) the second plurality of nodes, the third plurality of nodes, and/or the fourth plurality of nodes. In the same or other embodiments, the graph modeling system 100 may generate a plurality of multi-entity graph representations for one or more nodes of the nodes 502 and/or for one or more edges of the plurality of edges 504. In at least one embodiment, the graph modeling system 100 may utilize one or more tools or methods to automate and streamline generation, analysis, and utilization (e.g., as described below) of the multi-entity graph representation 506, thereby improving efficiency and scalability.

As further illustrated in FIG. 5, the graph modeling system 100 utilizes a graph neural network 508 to generate embeddings 510. As used herein the term "graph neural network" refers to a type of neural network/machine learning model that operates on graph-structured data. In particular, a graph neural network may be a self-supervised machine learning model or neural network, such as a graph attention model, that uses attention mechanisms to selectively weight the importance of neighboring nodes when learning representations for each node. For instance, a graph neural network can dynamically assign different attention weights to different edges or neighboring nodes based on their relevance or contribution to a target node's representation during the embedding process. As an example, a graph neural network may process nodes and edges of a multi-entity graph representation to generate embeddings by attending more strongly to nearby nodes with higher similarity, stronger edge weights, and/or shared entity-type relationships. In some cases, when processed by a graph neural network, each node may learn from neighboring nodes.

To elaborate, the graph modeling system 100 may use the multi-entity graph representation 506 as an input to the graph neural network 508 for generating the embeddings 510. In particular, the graph modeling system 100 may utilize the graph neural network 508 to process the multi-entity graph representation 506 and generate the embeddings 510 in a new latent space that enables comparison of the plurality of data entities corresponding to the nodes 502 and/or of the relationships between the data entities corresponding to the plurality of edges 504. For instance, the graph modeling system 100 may utilize the graph neural network 508 to generate one or more node embeddings for the embeddings 510, such as one or more of each of the following: clinical patient embeddings corresponding to patient nodes, compound embeddings corresponding to compound nodes, preclinical model embeddings corresponding to preclinical model nodes, and/or gene embeddings corresponding to gene nodes. In the same or other embodiments, the embeddings 510 may additionally or alternatively include other embeddings of biological entities or relationships, such as protein embeddings corresponding to protein nodes or signaling pathway embeddings corresponding to signaling pathway nodes. Thus, for instance, the graph modeling system 100 may generate a protein node and/or a signaling pathway node.

Further, the graph modeling system 100 may utilize the graph neural network 508 to generate one or more edge embeddings for the embeddings 510, such as one or more of each of the following: a gene-gene embedding corresponding to a gene-gene edge, a gene-compound embedding corresponding to a gene-compound edge, a compound-compound embedding corresponding to a compound-compound edge, a patient-patient embedding corresponding to a patient-patient edge, a patient-gene embedding corresponding to a patient-gene edge, a preclinical model-gene embedding corresponding to a preclinical model-gene edge, a preclinical model-compound embedding corresponding to a preclinical model-compound edge, preclinical model-preclinical model embedding corresponding to a preclinical model-preclinical model edge, and/or edge embeddings corresponding to edges that connect a protein node, signaling pathway node, and/or other biological entity or relationship node to another node of the nodes 502. Additionally or alternatively, the graph modeling system 100 may utilize the graph neural network 508 to generate one or more multi-entity graph representation embeddings for the embeddings 510 (e.g., one or more embeddings of the multi-entity graph representation 506 itself).

In one or more embodiments, the graph modeling system 100 may perform post-processing on the embeddings 510. For example, the graph modeling system 100 may apply a normalization operation (e.g., an L2 normalization operation) to the embeddings to ensure consistent scaling across nodes. Additionally or alternatively, the graph modeling system 100 may apply principal component analysis (PCA) to the embeddings and remove one or more leading principal components. In some cases, a leading principal component may reflect a node type, which can obscure biologically or clinically meaningful relationships across node types (e.g., by separating patient nodes from preclinical model nodes). By removing these leading principal components, the graph modeling system 100 can enhance the latent space to more effectively capture cross-entity similarities for improved therapeutic treatment determination and/or preclinical model identification.

As shown in FIG. 5, the graph modeling system 100 performs the act 512 for comparing the embeddings 510 generated from the multi-entity graph representation 506. In particular, the graph modeling system 100 may perform the act 512 to determine similarities or relationships between those entities, relationships, and/or multi-entity graph representations in a shared latent space. The graph modeling system 100 may perform the act 512 using one or more similarity metrics, such as cosine similarity, Euclidean distance, projection/rejection, and/or other vector-based distance measures. In some cases, the graph modeling system 100 may additionally utilize a continuous score and/or genetic score associated with one or more edges to inform or refine the comparison process.

As also shown in FIG. 5, the graph modeling system 100 may perform the act 512 to determine a therapeutic treatment 514 for one or more patients. As used herein, the term "therapeutic treatment" refers to an action, recommendation, and/or intervention intended to prevent, manage, and/or improve a clinical condition or disease in one or more patients. For instance, a therapeutic treatment can include determining a patient stratification of one or more clinical patients, where patient stratification can refer to refers to a process of dividing or classifying clinical patients into groups (for receiving particular treatments). In particular, patient stratification can involve selecting a subset of clinical patients based on patient classification features. In some cases, patient stratification includes patient enrichment, which can refer to a process of selecting or prioritizing a subset of clinical patients who are more likely to experience a favorable clinical outcome (e.g., an improved patient response) under a specific treatment condition like regulation of a target gene. In the same or other embodiments, a therapeutic treatment may include identifying or selecting a compound (e.g., drug) or combination of compounds (or agents) for administration to one or more clinical patients. Additionally or alternatively, a therapeutic treatment may include identifying alternative therapeutic modalities or personalizing treatment strategies based on learned similarities among clinical patients, compounds, preclinical models, and/or genes.

Specifically, to determine the therapeutic treatment 514, the graph modeling system 100 can compare a clinical patient embedding and one or more embeddings-such as one or more compound embeddings, preclinical model embeddings, gene embeddings, and/or additional clinical patient embeddings—to identify similarities within the latent space. To elaborate, the graph modeling system 100 may perform the act 512 to determine which patients of the plurality of clinical patients have a threshold level of similarity to a particular compound, preclinical model, gene, and/or to an additional clinical patient of the plurality of clinical patients. In at least one embodiment, the graph modeling system 100 may determine a plurality of therapeutic treatments for one or more patients.

For example, the graph modeling system 100 may compare one or more clinical patient embeddings and one or more preclinical model embeddings to determine which clinical patients are most similar to drug-sensitive or drug-resistant preclinical models. Based on this determination, the graph modeling system 100 may stratify the patient population into treatment-relevant subgroups for treatment. As another example, the system may compare one or more clinical patient embeddings to one or more compound embeddings to determine a therapeutic treatment likely to be effective for a particular patient or patient cohort. As yet another example, the graph modeling system 100 may compare one or more clinical patient embeddings to one or more gene embeddings to identify genes that are closely associated with a molecular or clinical profile of a clinical patient, which can inform therapeutic strategies such as targeting a specific gene or pathway with a corresponding drug or intervention. Additionally or alternatively, the graph modeling system 100 may compare one or more clinical patient embeddings to one or more additional clinical patient embeddings to identify patient subgroups with similar clinical or molecular characteristics, enabling patient stratification and guiding the selection of treatments shown or predicted to be effective in similar patients.

As illustrated in FIG. 5, the graph modeling system 100 can also determine other treatments or generate other predictions utilizing the embeddings 510. For example, the graph modeling system 100 can compare gene embeddings to determine gene similarity metrics for target identification in a drug discovery pipeline. Similarly, the graph modeling system 100 can compare compound embeddings (or compare compound and gene embeddings) to determine similarities for identifying drugs or gene targets in initiating drug discovery programs and/or validating selected compounds within a drug discovery program. The graph modeling system 100 can also compare compound embeddings with patient embeddings or pre-clinical embeddings to predict pre-clinical or clinical impacts/results of a compound. The graph modeling system 100 can also model different compounds at different concentrations (e.g., different nodes for different concentrations) to predict impacts of different concentrations across different interactions (e.g., compound-gene, compound-patient, compound-preclinical model interactions, results, or performance).

As further shown in FIG. 5, the graph modeling system 100 may perform the act 512 to identify a preclinical model 516 that is representative of a patient population. For instance, the graph modeling system 100 may identify the preclinical model 516 by comparing one or more clinical patient embeddings and one or more preclinical model embeddings to determine a clinical patient-preclinical model measure of similarity within a shared latent space. The graph modeling system 100 may then identify and/or select preclinical models whose embeddings are most similar to those of a patient population, such as if the graph modeling system 100 determines that a clinical patient-preclinical model measure of similarity satisfies a similarity threshold. In some cases, the graph modeling system 100 may identify the preclinical model 516 by comparing one or more preclinical model embeddings to one or more additional preclinical model embeddings to determine relative similarity among preclinical models. For example, the graph modeling system 100 may identify or selecting the model whose embedding exhibits the highest aggregate similarity to other preclinical model embeddings. In one or more embodiments, the graph modeling system 100 may identify a plurality of preclinical models.

In one or more embodiments, the graph modeling system 100 may generate one or more graphical user interfaces (GUIs) and/or one or more visualization tools. For instance, the graph modeling system 100 may generate and provide, for display on a client device, a GUI and/or visualization tools for visualizing, interpreting, and/or interacting with (e.g., modifying, accepting or rejecting, etc.) elements of the multi-entity graph representations, the embeddings 510, and/or results of the act 512 (e.g., therapeutic treatment determinations and/or preclinical model identifications). For instance, the graph modeling system 100 can provide a heatmap of similarities between nodes. Similarly, the graph modeling system 100 can receive selection of particular nodes and provide a similarity measure between the selected nodes.

Figure 6:
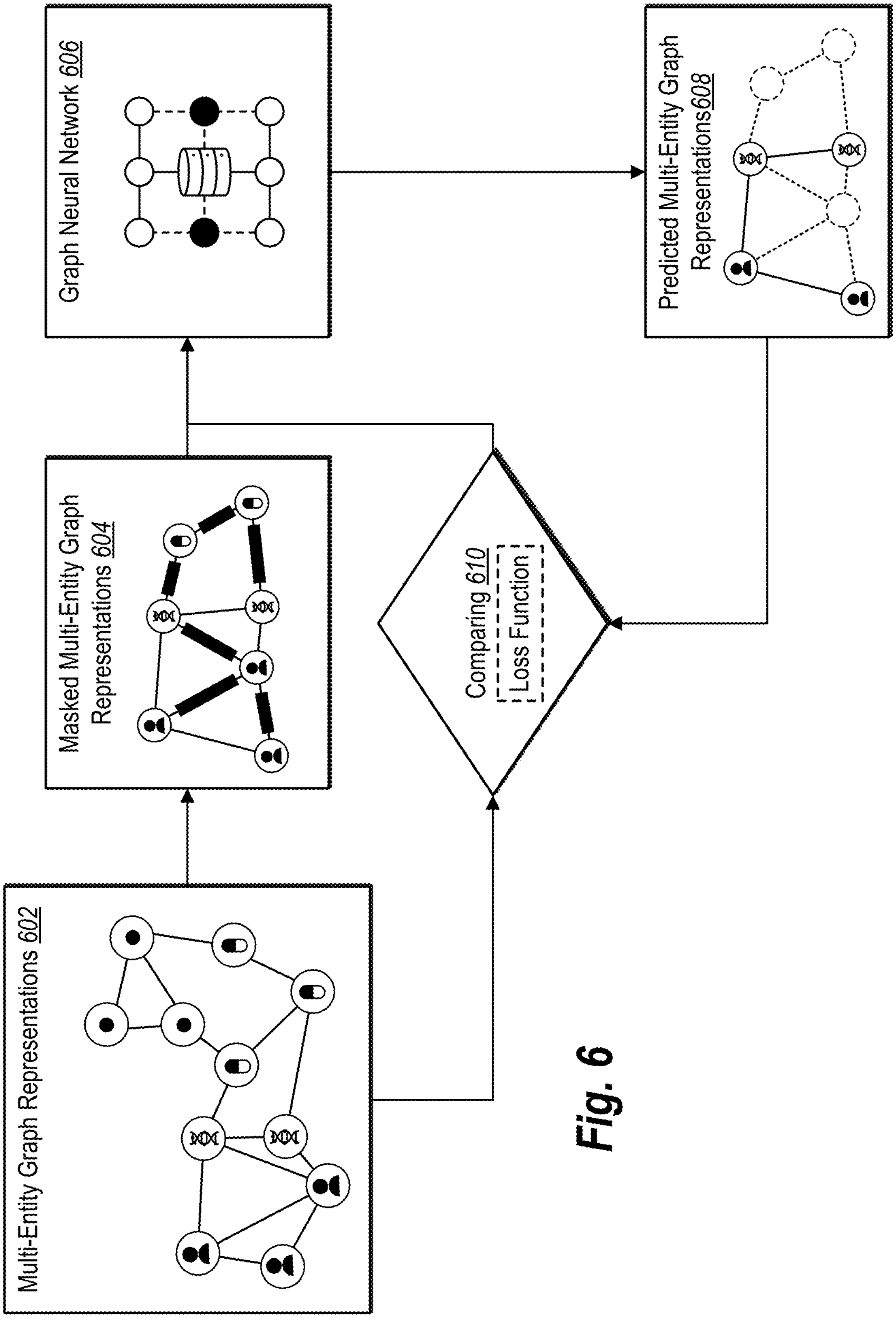
FIG. 6 illustrates an example diagram of a process for training (or fine-tuning) a graph neural network in accordance with one or more embodiments.

As expressed above, the graph modeling system 100 can train (or fine-tunes) a graph neural network. To elaborate, the graph modeling system 100 may use the graph neural network in a self-supervised setting to mask edges, edge weights, and/or edge features within a multi-entity graph representation, and prompt (or direct) the graph neural network to predict the edges, weights, and/or features of those masked edges. FIG. 6 illustrates an example diagram of a process for training (or fine-tuning) a graph neural network in accordance with one or more embodiments.

As illustrated in FIG. 6, the graph modeling system 100 utilizes multi-entity graph representations 602 to train (or fine tune) a graph neural network 606, such as a graph attention model. For instance, the graph modeling system 100 may generate the multi-entity graph representations 602 as described above in relation to FIG. 5. In one or more embodiments, the graph modeling system 100 may access, identify, or receive (e.g., from a database) the multi-entity graph representations 602 (e.g., as training multi-entity graph representations 602).

As also illustrated in FIG. 6, the graph modeling system 100 may generate masked multi-entity graph representations 604 from the multi-entity graph representations 602. For instance, the graph modeling system 100 may generate the masked multi-entity graph representations 604 by masking one or more edges, edge weights, and/or edge features of a subset of edges of the multi-entity graph representations 602. As shown in FIG. 6, the masked multi-entity graph representations may have masked edges and/or visible (or readable) edges of the plurality of edges of the multi-entity graph representations 602.

Additionally, as illustrated in FIG. 6, the graph modeling system 100 utilizes the masked multi-entity graph representations 604 as inputs to the graph neural network 606. In one or more embodiments, the graph neural network 606 may be as described above in relation to FIG. 5. In some instances, during training, the graph modeling system 100 utilizes the graph neural network 606 with the masked multi-entity graph representations 604 to generate, predict, or reconstruct predicted multi-entity graph representations 608. For example, to generate the predicted multi-entity graph representations 608, the graph modeling system 100 may utilize the graph neural network 606 to generate predicted edges, edge weights, and/or edge features for the subset of edges having masked edge weights. Accordingly, the graph modeling system 100 may utilize the graph neural network 606 to reconstruct the multi-entity graph representations 602 (as the predicted multi-entity graph representations 608) from the masked multi-entity graph representations 604.

Moreover, as illustrated in FIG. 6, the graph modeling system 100 performs the act 610 of comparing the predicted multi-entity graph representations 608 to the multi-entity graph representations 602. In particular, the graph modeling system 100 performs the act 610 using a loss function to determine a measure of loss. In some instances, the graph modeling system 100 may use the measure of loss to quantify errors (or inaccuracies) between the predicted multi-entity graph representations 608 and the original (ground truth) multi-entity graph representations 602. Indeed, the graph modeling system 100 utilizes the measure of loss with the graph neural network 606 to modify parameters of the graph neural network 606. For example, the graph modeling system 100 can iteratively generate predicted multi-entity graph representations 608 from the masked multi-entity graph representations 604 using the graph neural network 606 with modified parameters to reduce (or minimize) the measure of loss between the predicted edge weights of the predicted multi-entity graph representations 608 and the edge weights of the multi-entity graph representations 602.

Figure 7:
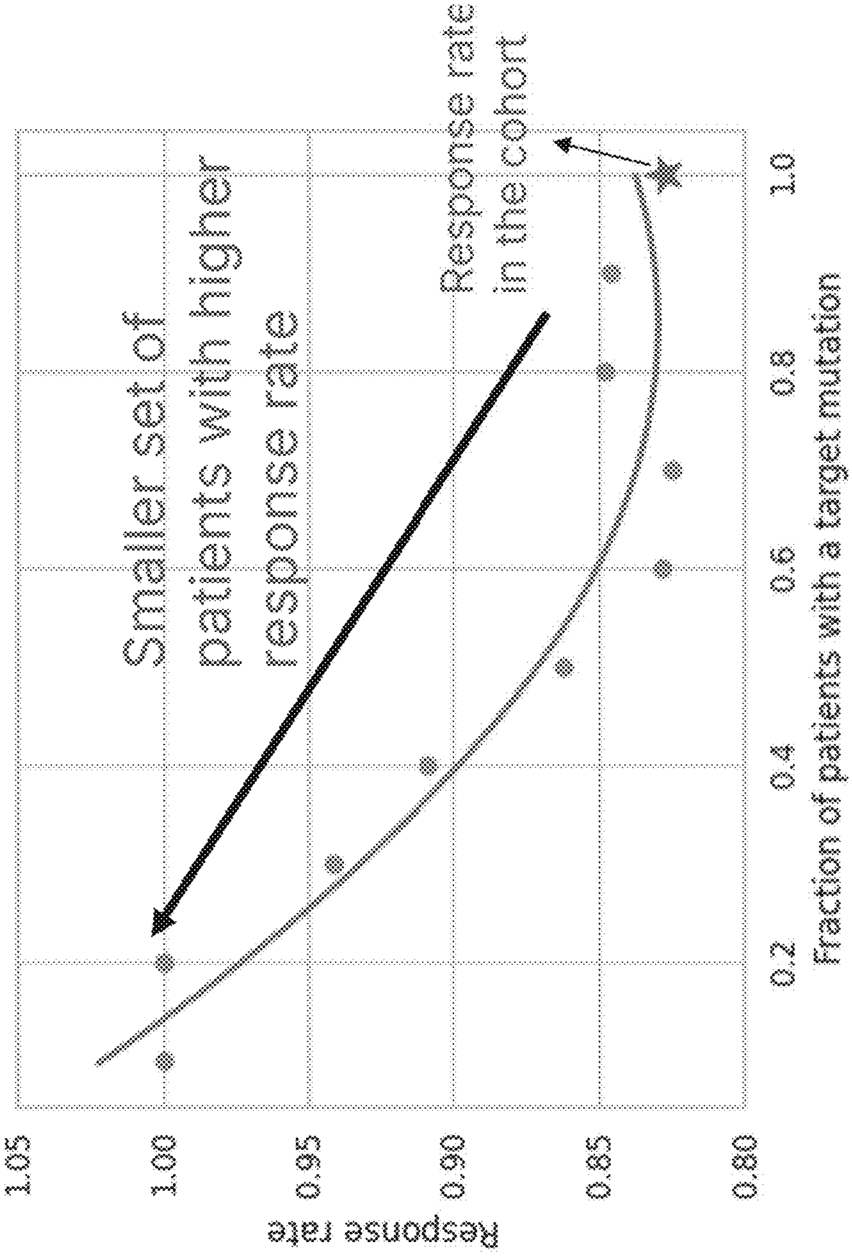
FIG. 7 illustrates an example data representation depicting identified patient responders to particular therapies in accordance with one or more embodiments.

As expressed above, the graph modeling system 100 may determine therapeutic treatments and/or identify preclinical models using multi-entity graph representations and a graph neural network. In particular, the graph modeling system 100 may determine a therapeutic treatment such as a patient stratification for one or more patients and/or identify a preclinical model that may be representative of a patient population. FIG. 7 illustrates an example data representation depicting identified patient responders to particular therapies in accordance with one or more embodiments.

As illustrated in FIG. 7, the graph modeling system 100 may identify responders to targeted therapies, such as a cancer therapy. For example, the graph modeling system 100 may identify responders by analyzing similarity between clinical patient embeddings and preclinical model embeddings (e.g., labeled as sensitive or resistant to a given compound). In some cases, the graph modeling system 100 may identify responders based on determining that they have a higher similarity. As shown in FIG. 7, each data point represents a quantile of patients grouped according to their relative similarity to compound-sensitive versus compound-resistant cell lines. For each quantile, the graph modeling system 100 may compute an associated response rate to a therapy, revealing a relationship between a clinical patient-preclinical model measure of similarity and an observed therapeutic response. As also shown in FIG. 7, a fitted curve may be used to model the fraction of patients with a target mutation and response rate. In some cases, by using the above analysis, the graph modeling system 100 may determine a therapeutic treatment and/or identify a preclinical model that is representative of a patient population. In the same or other embodiments, the graph modeling system 100 may handle complexities of defining therapy-specific response outcomes such as by incorporating time-to-progression or other relevant clinical endpoints.

In some embodiments, the graph modeling system 100 is part of a networking environment. For example, FIG. 8 illustrates a diagram of an example environment in which the graph modeling system 100 can operate in accordance with one or more embodiments.

Figure 8:
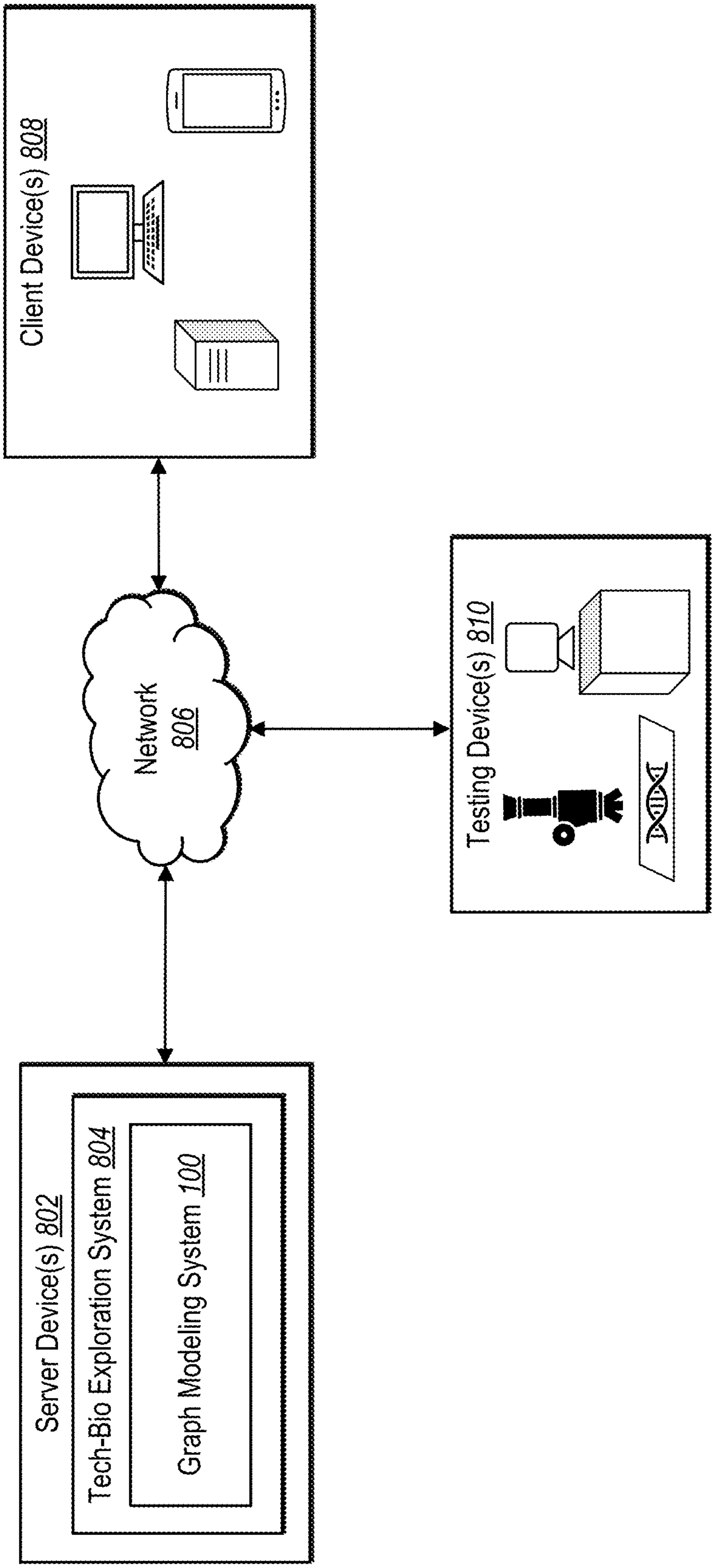
FIG. 8 illustrates a diagram of an example environment in which a graph modeling system can operate in accordance with one or more embodiments.

As shown in FIG. 8, the environment includes server device(s) 802 (which includes a tech-bio exploration system 804 and the graph modeling system 100), a network 806, client device(s) 808, and testing device(s) 810. As further illustrated in FIG. 8, the various computing devices within the environment can communicate via the network 806. In the same or other embodiments, the server device(s) 802, the client device(s) 808, and/or the testing device(s) 810 may send to, receive from, and/or access one or more functional response machine learning embeddings, digital clinical datasets (e.g., the digital clinical dataset 302), and/or digital preclinical-model datasets (e.g., the digital preclinical-model dataset 402), such as via the network 806 or without the network 806. Although FIG. 8 illustrates the graph modeling system 100 being implemented by a particular component and/or device within the environment, the graph modeling system 100 can be implemented, in whole or in part, by other computing devices and/or components in the environment (e.g., the client device(s) 808). Additional description regarding the illustrated computing devices is provided with respect to FIG. 10 below.

As shown in FIG. 8, the server device(s) 802 can include the tech-bio exploration system 804. In some embodiments, the tech-bio exploration system 804 can determine, store, generate, analyze and/or display tech-bio information including maps of biology, biology experiments from various sources, and/or machine learning tech-bio predictions. For instance, the tech-bio exploration system 804 can analyze data signals corresponding to various treatments or interventions (e.g., compounds or biologics) and the corresponding relationships in genetics, proteomics, phenomics (i.e., cellular phenotypes), and invivomics (e.g., expressions or results within a living animal). In one or more embodiments, the server device(s) 802 comprises a data server. In some implementations, the server device(s) 802 comprises a communication server or a web-hosting server.

Further, the tech-bio exploration system 804 can generate and access experimental results corresponding to gene sequences, protein shapes/folding, protein/compound interactions, phenotypes resulting from various interventions or perturbations (e.g., gene knockout sequences or compound treatments), and/or in vivo experimentation on various treatments in living animals. By analyzing these signals (e.g., utilizing various machine learning models), the tech-bio exploration system 804 can generate or determine a variety of predictions and inter-relationships for improving treatments/interventions.

To illustrate, the tech-bio exploration system 804 can generate maps of biology indicating biological inter-relationships or similarities between these various input signals to discover potential new treatments. For example, the tech-bio exploration system 804 can utilize machine learning and/or maps of biology to identify a similarity between a first gene associated with disease treatment and a second gene previously unassociated with the disease based on a similarity in resulting phenotypes from gene knockout experiments. The tech-bio exploration system 804 can then identify new treatments based on the gene similarity (e.g., by targeting compounds the impact the second gene). Similarly, the tech-bio exploration system 804 can analyze signals from a variety of sources (e.g., protein interactions, or in vivo experiments) to predict efficacious treatments based on various levels of biological data.

The tech-bio exploration system 804 can generate GUIs comprising dynamic user interface elements to convey tech-bio information and receive user input for intelligently exploring tech-bio information. Indeed, as mentioned above, the tech-bio exploration system 804 can generate GUIs displaying different maps of biology that intuitively and efficiently express complex interactions between different biological systems for identifying improved treatment solutions. Furthermore, the tech-bio exploration system 804 can also electronically communicate tech-bio information between various computing devices.

As shown in FIG. 8, the tech-bio exploration system 804 can include a system that facilitates various models or algorithms for generating maps of biology (e.g., maps or visualizations-such as multi-entity graph representations-illustrating similarities or relationships between clinical patients, genes, proteins, diseases, compounds, and/or treatments) and discovering new treatment options (e.g., therapeutic treatments, including patient stratification) over one or more networks. For example, the tech-bio exploration system 804 collects, manages, and transmits data across a variety of different entities, accounts, and devices. In some cases, the tech-bio exploration system 804 is a network system that facilitates access to (and analysis of) tech-bio information within a centralized operating system. Indeed, the tech-bio exploration system 804 can link data from different network-based research institutions to generate and analyze maps of biology and/or multi-entity graph representations.

As shown in FIG. 8, the tech-bio exploration system 804 can include a system that comprises the graph modeling system 100 that generates, stores, manages, transmits, and analyzes cell and subject perturbation datasets. For example, the graph modeling system 100 can generate perturbation experiment unit embeddings utilizing a machine learning model and synthesize the embeddings according to various filtration, alignment, and aggregation models. Further, the graph modeling system 100 can identify similarity measures between aggregated perturbation embeddings (e.g., perturbation-level embeddings) of a perturbation embedding model and determine a benchmark measure for the perturbation embedding model. For example, the graph modeling system 100 can generate a transcriptomic benchmark for the perturbation experiment unit embeddings of the perturbation embedding model and/or a transcriptomic benchmark for the identified similarity measures for display.

As also illustrated in FIG. 8, the environment includes the client device(s) 808. For example, the client device(s) 808 may include, but is not limited to, a mobile device (e.g., smartphone, tablet) or other type of computing device, including those explained below with reference to FIG. 10. Additionally, the client device(s) 808 can include a computing device associated with (and/or operated by) user accounts for the tech-bio exploration system 804. Moreover, the environment can include various numbers of client devices that communicate and/or interact with the tech-bio exploration system 804 and/or the graph modeling system 100.

Furthermore, in one or more implementations, the client device(s) 808 includes a client application. The client application can include instructions that (upon execution) cause the client device(s) 808 to perform various actions. For example, a user of a user account can interact with the client application on the client device(s) 808 to access or generating multi-entity graph representations, access tech-bio information, initiate a request for a benchmark measure, to access or generate maps of biology, and/or generate GUIs comprising similarity measures, benchmark measures, or other machine learning dataset and/or machine learning predictions/results. In one or more embodiments, a user of a user account may additionally or alternatively interact with the client application on the client device(s) 808 to provide for display one or more results, including multi-entity graph representations, embeddings (e.g., node embeddings, edge embeddings, and/or multi-entity graph representation embeddings), functional response machine learning embeddings (and/or functional response maps), digital clinical dataset data, digital preclinical-model dataset data, treatment variables, therapeutic treatments (e.g., patient stratifications), gene signatures, and/or identified preclinical models.

As further shown in FIG. 8, the environment includes the network 806. As mentioned above, the network 806 can enable communication between components of the environment. In one or more embodiments, the network 806 may include a suitable network and may communicate using a various number of communication platforms and technologies suitable for transmitting data and/or communication signals, examples of which are described with reference to FIG. 10. Furthermore, although FIG. 8 illustrates computing devices communicating via the network 806, the various components of the environment can communicate and/or interact via other methods (e.g., communicate directly).

As mentioned previously, in one or more implementations, the graph modeling system 100 generates and accesses machine learning objects, such as results from biological assays, in vivo trials, results from perturbation embedding models, etc. As shown, in FIG. 8, the graph modeling system 100 can communicate with testing device(s) 810 to obtain and then store this information. For example, the tech-bio exploration system 804 can interact with the testing device(s) 810 that include intelligent robotic devices and camera devices for generating and capturing digital images of cellular phenotypes resulting from different perturbations (e.g., genetic knockouts or compound treatments of stem cells). Similarly, the testing device(s) can include camera devices and/or other sensors (e.g., heat or motion sensors) capturing real-time information from animals as part of in vivo experimentation. The tech-bio exploration system 804 can also interact with a variety of other testing device(s) such as devices for determining, generating, or extracting gene sequences or protein information.

Figure 9:
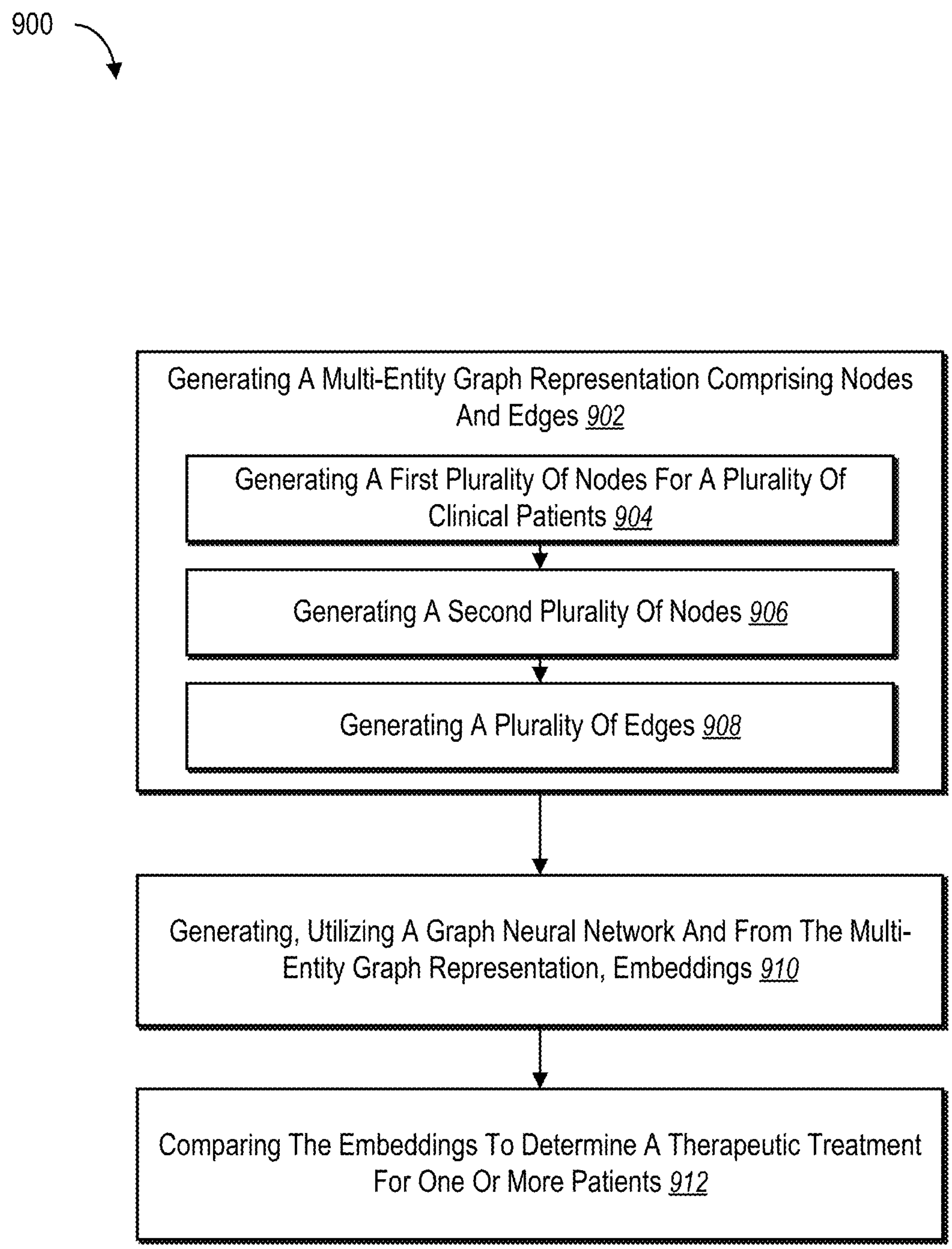
FIG. 9 illustrates an example flowchart of a series of acts for determining a therapeutic treatment for one or more patients in accordance with one or more embodiments.

FIGS. 1-8, the corresponding text, and the examples provide a number of different systems and methods for determining a therapeutic treatment for one or more patients. In addition to the foregoing, implementations can also be described in terms of flowcharts comprising acts steps in a method for accomplishing a particular result. For example, FIG. 9 illustrates an example flowchart of a series of acts for determining a therapeutic treatment for one or more patients in accordance with one or more embodiments. While FIG. 9 illustrates acts according to certain implementations, alternative implementations may omit, add to, reorder, and/or modify any of the acts shown in FIG. 9. The acts of FIG. 9 can be performed as part of a method (e.g., a computer-implemented method). Alternatively, a non-transitory computer readable medium can comprise instructions that, when executed by one or more processors, cause a computing device to perform the acts of FIG. 9. In still further implementations, a system can perform the acts of FIG. 9. Additionally, the acts described herein may be repeated or performed in parallel with one another or in parallel with different instances of the same or other similar acts.

As illustrated in FIG. 9, the series of acts 900 may include an act 902 of generating a multi-entity graph representation comprising nodes and edges by performing acts 904, 906, and 908. The series of acts 900 can also include the act 904 of generating a first plurality of nodes for a plurality of clinical patients. In particular, the act 904 can involve generating a first plurality of nodes for a plurality of clinical patients from a digital clinical dataset. Additionally, the series of acts 900 can include the act 906 of generating a second plurality of nodes. In particular, the act 906 can involve generating a second plurality of nodes, wherein the second plurality of nodes comprise at least one of: compound nodes, preclinical model nodes, or gene nodes. Further, the series of acts 900 can include the act 908 of generating a plurality of edges. In particular, the act 908 can involve generating a plurality of edges by encoding relationships between the nodes into the edges. In some embodiments, the series of acts 900 may include an act 910 of generating, utilizing a graph neural network and from the multi-entity graph representation, embeddings. Specifically, the act 910 may involve generating, utilizing a graph neural network and from the multi-entity graph representation, embeddings comprising a clinical patient embedding and at least one of: a compound embedding, a preclinical model embedding, a gene embedding, or an additional clinical patient embedding. In addition, the series of acts 900 may include an act 912 of comparing the embeddings to determine a therapeutic treatment for one or more patients. In particular, the act 912 may involve comparing the clinical patient embedding and at least one of the compound embedding, the preclinical model embedding, the gene embedding, or the additional clinical patient embedding to determine a therapeutic treatment for one or more patients of the plurality of clinical patients.

In some embodiments, the series of acts 900 includes an act of generating the plurality of edges by generating a patient-patient edge between a first patient node and a second patient node of the first plurality of nodes by: generating a first clinical feature representation for a first clinical patient corresponding to the first patient node; generating a second clinical feature representation for a second clinical patient corresponding to the second patient node; and generating the patient-patient edge based on a distance between the first clinical feature representation and the second clinical feature representation. The series of acts 900 can also include an act of generating the plurality of edges by generating a patient-gene edge between a patient node of the first plurality of nodes and a gene node of the second plurality of nodes by: identifying a gene expression metric of a patient corresponding to the patient node with respect to a gene corresponding to the gene node; and generating the patient-gene edge based on the gene expression metric.

In some embodiments, the series of acts 900 includes an act of generating the plurality of edges by generating a gene-gene edge between a first gene node and a second gene node of the gene nodes by: generating, utilizing a machine learning model, a first gene functional response machine learning embedding for a first gene corresponding to the first gene node from a first transcriptomic profile or a first phenomic image of a first cell exposed to a gene knockout of the first gene; generating, utilizing the machine learning model, a second gene functional response machine learning embedding for a second gene corresponding to the second gene node from a second transcriptomic profile or a second phenomic image of a second cell exposed to an additional gene knockout of the second gene; and generating the gene-gene edge between the first gene node and the second gene node by comparing the first gene functional response machine learning embedding and the second gene functional response machine learning embedding. In the same or other embodiments, the series of acts 900 includes an act of generating the plurality of edges by generating a gene-compound edge between the first gene node and a compound node of the second plurality of nodes by: generating, utilizing the machine learning model, a compound functional response machine learning embedding for a compound corresponding to the compound node from a third transcriptomic profile or a third phenomic image of a cell exposed to the compound; and generating the gene-compound edge between the first gene node and the compound node by comparing the first gene functional response machine learning embedding and the compound functional response machine learning embedding.

In one or more embodiments, the series of acts 900 includes an act of generating the plurality of edges comprises generating a preclinical model-gene edge between a preclinical model node of the second plurality of nodes and a gene node of the second plurality of nodes by: identifying a gene expression metric from preclinical model sensitivity data of a cell line or xenograft exposed to a perturbation; and generating the preclinical model-gene edge based on the gene expression metric. The series of acts 900 can also include an act of training the graph neural network by:

masking edge weights of a subset of the plurality of edges; generating, utilizing the graph neural network, predicted edge weights for the subset of the plurality of edges; and modifying one or more parameters of the graph neural network based on a loss between the edge weights and the predicted edge weights.

In at least one embodiment, the series of acts 900 may include an act of determining the therapeutic treatment comprises determining a patient stratification of the one or more patients of the plurality of patients based on comparing the clinical patient embedding and at least one of the compound embedding, the preclinical model embedding, the gene embedding, or the additional clinical patient embedding. Further, the series of acts 900 may include an act of comparing the clinical patient embedding and the preclinical model embedding to determine a clinical patient-preclinical model measure of similarity; and identifying a preclinical model representative of a patient population based on determining that clinical patient-preclinical model measure of similarity satisfies a similarity threshold.

In one or more embodiments, the series of acts 900 may include an act of generating the plurality of edges by generating at least one of: a patient-patient edge between a first patient node and a second patient node of the first plurality of nodes; or a patient-gene edge between a patient node of the first plurality of nodes and a gene node of the second plurality of nodes. Additionally, the series of acts 900 may include an act of generating the plurality of edges by generating at least one of: a gene-gene edge between a first gene node and a second gene node of the gene nodes; a gene-compound edge between the first gene node and a compound node of the second plurality of nodes; or a preclinical model-gene edge between a preclinical model node of the second plurality of nodes and a gene node of the second plurality of nodes.

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., memory), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some embodiments, computer-executable instructions are executed by a general-purpose computer to turn the general-purpose computer into a special purpose computer implementing elements of the disclosure. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present disclosure can also be implemented in cloud computing environments. As used herein, the term "cloud computing" refers to a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In addition, as used herein, the term "cloud-computing environment" refers to an environment in which cloud computing is employed.

Figure 10:
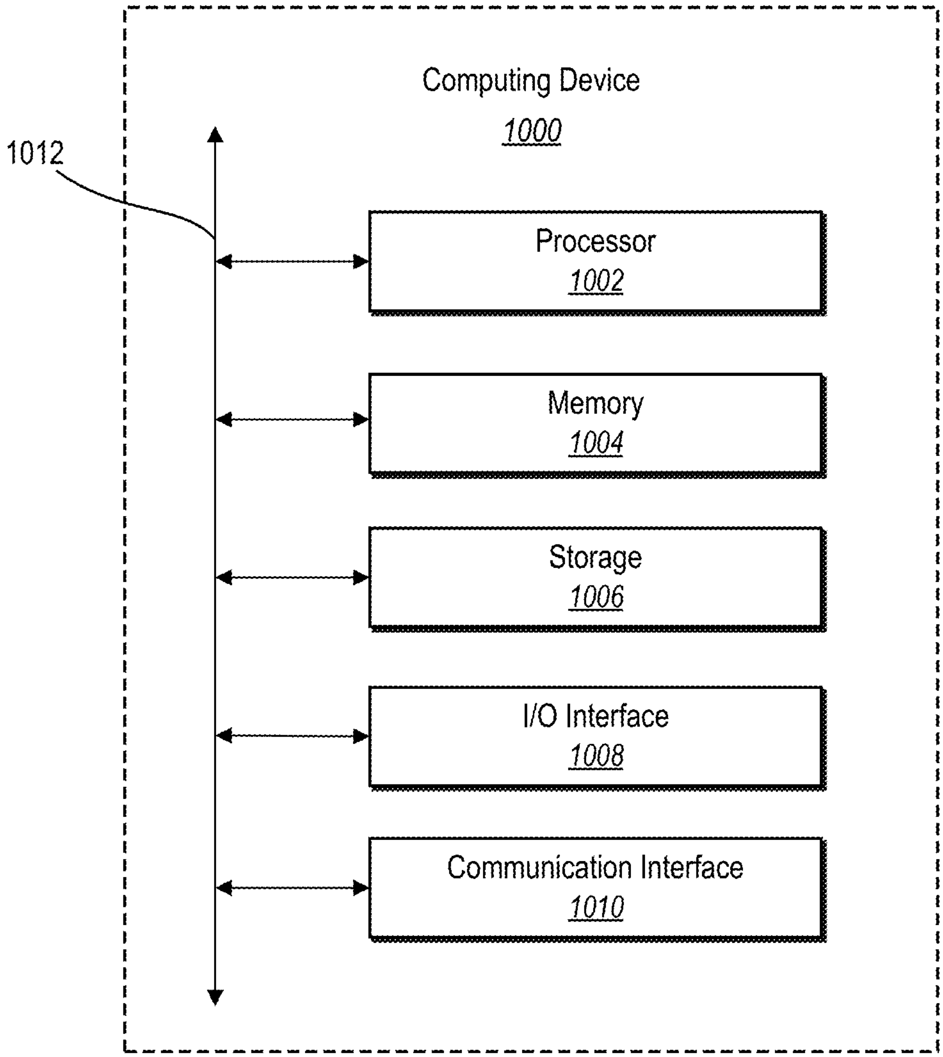
FIG. 10 illustrates a block diagram of an exemplary computing device in accordance with one or more embodiments.

FIG. 10 illustrates a block diagram of an example computing device 1000 that may be configured to perform one or more of the processes described above. One will appreciate that one or more computing devices, such as the computing device 1000 may represent the computing devices described above. In one or more embodiments, the computing device 1000 may be a mobile device (e.g., a mobile telephone, a smartphone, a PDA, a tablet, a laptop, a camera, a tracker, a watch, a wearable device, etc.). In some embodiments, the computing device 1000 may be a non-mobile device (e.g., a desktop computer or another type of client device). Further, the computing device 1000 may be a server device that includes cloud-based processing and storage capabilities.

As shown in FIG. 10, the computing device 1000 can include one or more processor(s) 1002, memory 1004, a storage device 1006, input/output interfaces 1008 (or "I/O interfaces 1008"), and a communication interface 1010, which may be communicatively coupled by way of a communication infrastructure (e.g., bus 1012). While the computing device 1000 is shown in FIG. 10, the components illustrated in FIG. 10 are not intended to be limiting. Additional or alternative components may be used in other embodiments. Furthermore, in certain embodiments, the computing device 1000 includes fewer components than those shown in FIG. 10. Components of the computing device 1000 shown in FIG. 10 will now be described in additional detail.

In particular embodiments, the processor(s) 1002 includes hardware for executing instructions, such as those making up a computer program. As an example, and not by way of limitation, to execute instructions, the processor(s) 1002 may retrieve (or fetch) the instructions from an internal register, an internal cache, memory 1004, or a storage device 1006 and decode and execute them.

The computing device 1000 includes memory 1004, which is coupled to the processor(s) 1002. The memory 1004 may be used for storing data, metadata, and programs for execution by the processor(s). The memory 1004 may include one or more of volatile and non-volatile memories, such as Random-Access Memory ("RAM"), Read-Only Memory ("ROM"), a solid-state disk ("SSD"), Flash, Phase Change Memory ("PCM"), or other types of data storage. The memory 1004 may be internal or distributed memory.

The computing device 1000 includes a storage device 1006 includes storage for storing data or instructions. As an example, and not by way of limitation, the storage device 1006 can include a non-transitory storage medium described above. The storage device 1006 may include a hard disk drive (HDD), flash memory, a Universal Serial Bus (USB) drive or a combination these or other storage devices.

As shown, the computing device 1000 includes one or more I/O interfaces 1008, which are provided to allow a user to provide input to (such as user strokes), receive output from, and otherwise transfer data to and from the computing device 1000. These I/O interfaces 1008 may include a mouse, keypad or a keyboard, a touch screen, camera, optical scanner, network interface, modem, other known I/O devices or a combination of such I/O interfaces 1008. The touch screen may be activated with a stylus or a finger.

The I/O interfaces 1008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O interfaces 1008 are configured to provide graphical data to a display for presentation to a user. The graphical data may be representative of one or more graphical user interfaces and/or any other graphical content as may serve a particular implementation.

The computing device 1000 can further include a communication interface 1010. The communication interface 1010 can include hardware, software, or both. The communication interface 1010 provides one or more interfaces for communication (such as, for example, packet-based communication) between the computing device and one or more other computing devices or one or more networks. As an example, and not by way of limitation, communication interface 1010 may include a network interface controller (NIC) or network adapter for communicating with an Ethernet or other wire-based network or a wireless NIC (WNIC) or wireless adapter for communicating with a wireless network, such as a WI-FI. The computing device 1000 can further include a bus 1012. The bus 1012 can include hardware, software, or both that connects components of computing device 1000 to each other.

In one or more implementations, various computing devices can communicate over a computer network. This disclosure contemplates any suitable network. As an example, and not by way of limitation, one or more portions of a network may include an ad hoc network, an intranet, an extranet, a virtual private network ("VPN"), a local area network ("LAN"), a wireless LAN ("WLAN"), a wide area network ("WAN"), a wireless WAN ("WWAN"), a metropolitan area network ("MAN"), a portion of the Internet, a portion of the Public Switched Telephone Network ("PSTN"), a cellular telephone network, or a combination of two or more of these.

In particular embodiments, the computing device 1000 can include a client device that includes a requester application or a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user at the client device may enter a Uniform Resource Locator ("URL") or other address directing the web browser to a particular server (such as server), and the web browser may generate a Hyper Text Transfer Protocol ("HTTP")

request and communicate the HTTP request to server. The server may accept the HTTP request and communicate to the client device one or more Hyper Text Markup Language ("HTML") files responsive to the HTTP request. The client device may render a webpage based on the HTML files from the server for presentation to the user. This disclosure contemplates any suitable webpage files. As an example, and not by way of limitation, webpages may render from HTML files, Extensible Hyper Text Markup Language ("XHTML") files, or Extensible Markup Language ("XML") files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, the tech-bio exploration system 804 may include a variety of servers, sub-systems, programs, modules, logs, and data stores. In particular embodiments, the tech-bio exploration system 804 may include one or more of the following: a web server, action logger, API-request server, transaction engine, cross-institution network interface manager, notification controller, action log, third-party-content-object-exposure log, inference module, authorization/privacy server, search module, user-interface module, user-profile (e.g., provider profile or requester profile) store, connection store, third-party content store, or location store. The tech-bio exploration system 804 may also include suitable components such as network interfaces, security mechanisms, load balancers, failover servers, management-and-network-operations consoles, other suitable components, or any suitable combination thereof. In particular embodiments, the tech-bio exploration system 804 may include one or more user-profile stores for storing user profiles and/or account information for credit accounts, secured accounts, secondary accounts, and other affiliated financial networking system accounts. A user profile may include, for example, biographic information, demographic information, financial information, behavioral information, social information, or other types of descriptive information, such as interests, affinities, or location.

The web server may include a mail server or other messaging functionality for receiving and routing messages between the tech-bio exploration system 804 and one or more client devices. An action logger may be used to receive communications from a web server about a user's actions on or off the tech-bio exploration system 804. In conjunction with the action log, a third-party-content-object log may be maintained of user exposures to third-party-content objects. A notification controller may provide information regarding content objects to a client device. Information may be pushed to a client device as notifications, or information may be pulled from a client device responsive to a request received from the client device. Authorization servers may be used to enforce one or more privacy settings of the users of the tech-bio exploration system 804. A privacy setting of a user determines how particular information associated with a user can be shared. The authorization server may allow users to opt in to or opt out of having their actions logged by the tech-bio exploration system 804 or shared with other systems, such as, for example, by setting appropriate privacy settings. Third-party-content-object stores may be used to store content objects received from third parties. Location stores may be used for storing location information received from a client device associated with users.

In the foregoing specification, the invention has been described with reference to specific example embodiments thereof. Various embodiments and aspects of the invention(s) are described with reference to details discussed herein, and the accompanying drawings illustrate the various embodiments. The description above and drawings are illustrative of the invention and are not to be construed as limiting the invention. Numerous specific details are described to provide a thorough understanding of various embodiments of the present invention.

The present invention may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A computer-implemented method comprising:

generating a multi-entity graph representation comprising nodes and edges by:

generating a first plurality of nodes for a plurality of clinical patients from a digital clinical dataset;

generating a second plurality of nodes for a plurality of genes;

generating a third plurality of nodes comprising at least one of: compound nodes for a plurality of compounds or preclinical model nodes for a plurality of preclinical models from a digital preclinical-model dataset; and generating a plurality of edges by encoding relationships between the nodes into the edges, wherein generating the plurality of edges comprises generating a gene-gene edge between gene nodes of the second plurality of nodes representing genes from cells exposed to a perturbation by:

generating, utilizing a machine learning model, functional response machine learning embeddings for genes corresponding to the gene nodes, the functional response machine learning embeddings comprising one or more phenomic embeddings or transcriptomic embeddings; and generating the gene-gene edge between the gene nodes by determining a similarity measure between the functional response machine learning embeddings;

generating, utilizing a graph neural network and from the multi-entity graph representation, embeddings in a shared latent space, wherein the embeddings comprise a clinical patient embedding and at least one of: a compound embedding, a preclinical model embedding, a gene embedding, or an additional clinical patient embedding; and comparing the clinical patient embedding and at least one of the compound embedding, the preclinical model embedding, the gene embedding, or the additional clinical patient embedding to determine a therapeutic treatment for one or more patients of the plurality of clinical patients.

2. The computer-implemented method of claim 1, wherein generating the plurality of edges comprises generating a patient-patient edge between a first patient node and a second patient node of the first plurality of nodes by:

generating a first clinical feature representation for a first clinical patient corresponding to the first patient node;

generating a second clinical feature representation for a second clinical patient corresponding to the second patient node; and generating the patient-patient edge based on a distance between the first clinical feature representation and the second clinical feature representation.

3. The computer-implemented method of claim 1, wherein generating the plurality of edges comprises generating a patient-gene edge between a patient node of the first plurality of nodes and a gene node of the second plurality of nodes by:

identifying a gene expression metric of a patient corresponding to the patient node with respect to a gene corresponding to the gene node; and generating the patient-gene edge based on the gene expression metric.

4. The computer-implemented method of claim 1, wherein generating the gene-gene edge between gene nodes of the second plurality of nodes comprises generating an edge between a first gene node and a second gene node of the second plurality of nodes by:

generating, utilizing a machine learning model, a first gene functional response machine learning embedding for a first gene corresponding to the first gene node from a first transcriptomic profile or a first phenomic image of a first cell exposed to a gene knockout of the first gene;

generating, utilizing the machine learning model, a second gene functional response machine learning embedding for a second gene corresponding to the second gene node from a second transcriptomic profile or a second phenomic image of a second cell exposed to an additional gene knockout of the second gene; and generating the edge between the first gene node and the second gene node by comparing the first gene functional response machine learning embedding and the second gene functional response machine learning embedding.

5. The computer-implemented method of claim 4, wherein generating the plurality of edges comprises generating a gene-compound edge between the first gene node and a compound node of the third plurality of nodes by:

generating, utilizing the machine learning model, a compound functional response machine learning embedding for a compound corresponding to the compound node from a third transcriptomic profile or a third phenomic image of a cell exposed to the compound; and generating the gene-compound edge between the first gene node and the compound node by comparing the first gene functional response machine learning embedding and the compound functional response machine learning embedding.

6. The computer-implemented method of claim 1, wherein generating the plurality of edges comprises generating a preclinical model-gene edge between a preclinical model node of the third plurality of nodes and a gene node of the second plurality of nodes by:

identifying a gene expression metric from preclinical model sensitivity data of a cell line or xenograft exposed to a perturbation; and generating the preclinical model-gene edge based on the gene expression metric.

7. The computer-implemented method of claim 1, further comprising training the graph neural network by:

masking edge weights of a subset of the plurality of edges;

generating, utilizing the graph neural network, predicted edge weights for the subset of the plurality of edges; and modifying one or more parameters of the graph neural network based on a loss between the edge weights and the predicted edge weights.

8. The computer-implemented method of claim 1, wherein determining the therapeutic treatment comprises determining a patient stratification of the one or more patients of the plurality of clinical patients based on comparing the clinical patient embedding and at least one of the compound embedding, the preclinical model embedding, the gene embedding, or the additional clinical patient embedding.

9. The computer-implemented method of claim 1, further comprising:

comparing the clinical patient embedding and the preclinical model embedding to determine a clinical patient-preclinical model measure of similarity; and identifying a preclinical model representative of a patient population based on determining that clinical patient-preclinical model measure of similarity satisfies a similarity threshold.

10. A system comprising:

at least one processor; and at least one non-transitory computer-readable storage medium storing instructions that, when executed by the at least one processor, cause the system to:

generate a multi-entity graph representation comprising nodes and edges by:

generating a first plurality of nodes for a plurality of clinical patients from a digital clinical dataset;

generating a second plurality of nodes for a plurality of genes;

generating a third plurality of nodes comprising at least one of: compound nodes for a plurality of compounds or preclinical model nodes for a plurality of preclinical models from a digital preclinical-model dataset; and generating a plurality of edges by encoding relationships between the nodes into the edges, wherein generating the plurality of edges comprises generating a gene-gene edge between gene nodes of the second plurality of nodes representing genes from cells exposed to a perturbation by:

generating, utilizing a machine learning model, functional response machine learning embeddings for genes corresponding to the gene nodes, the functional response machine learning embeddings comprising one or more phenomic embeddings or transcriptomic embeddings; and generating the gene-gene edge between the gene nodes by determining a similarity measure between the functional response machine learning embeddings;

generate, utilizing a graph neural network and from the multi-entity graph representation, embeddings in a shared latent space, wherein the embeddings comprise a clinical patient embedding and at least one of: a compound embedding, a preclinical model embedding, a gene embedding, or an additional clinical patient embedding; and compare the clinical patient embedding and at least one of the compound embedding, the preclinical model embedding, the gene embedding, or the additional clinical patient embedding to determine a therapeutic treatment for one or more patients of the plurality of clinical patients.

11. The system of claim 10, further comprising instructions that, when executed by the at least one processor, cause the system to generate the plurality of edges by generating a patient-patient edge between a first patient node and a second patient node of the first plurality of nodes by:

generating a first clinical feature representation for a first clinical patient corresponding to the first patient node;

generating a second clinical feature representation for a second clinical patient corresponding to the second patient node; and generating the patient-patient edge based on a distance between the first clinical feature representation and the second clinical feature representation.

12. The system of claim 10, further comprising instructions that, when executed by the at least one processor, cause the system to generate the gene-gene edge between gene nodes of the second plurality of nodes by generating an edge between a first gene node and a second gene node of the second plurality of nodes by:

generating, utilizing a machine learning model, a first gene functional response machine learning embedding for a first gene corresponding to the first gene node from a first transcriptomic profile or a first phenomic image of a first cell exposed to a gene knockout of the first gene;

generating, utilizing the machine learning model, a second gene functional response machine learning embedding for a second gene corresponding to the second gene node from a second transcriptomic profile or a second phenomic image of a second cell exposed to an additional gene knockout of the second gene; and generating the edge between the first gene node and the second gene node by comparing the first gene functional response machine learning embedding and the second gene functional response machine learning embedding.

13. The system of claim 12, further comprising instructions that, when executed by the at least one processor, cause the system to generate a gene-compound edge between the first gene node and a compound node of the third plurality of nodes by:

generating, utilizing the machine learning model, a compound functional response machine learning embedding for a compound corresponding to the compound node from a third transcriptomic profile or a third phenomic image of a cell exposed to the compound; and generating the gene-compound edge between the first gene node and the compound node by comparing the first gene functional response machine learning embedding and the compound functional response machine learning embedding.

14. The system of claim 10, further comprising instructions that, when executed by the at least one processor, cause the system to generate the plurality of edges by generating a preclinical model-gene edge between a preclinical model node of the third plurality of nodes and a gene node of the second plurality of nodes by:

identifying a gene expression metric from preclinical model sensitivity data of a cell line or xenograft exposed to a perturbation; and generating the preclinical model-gene edge based on the gene expression metric.

15. The system of claim 10, further comprising instructions that, when executed by the at least one processor, cause the system to train the graph neural network by:

masking edge weights of a subset of the plurality of edges;

generating, utilizing the graph neural network, predicted edge weights for the subset of the plurality of edges; and modifying one or more parameters of the graph neural network based on a loss between the edge weights and the predicted edge weights.

16. The system of claim 10, further comprising instructions that, when executed by the at least one processor, cause the system to determine the therapeutic treatment by determining a patient stratification of the one or more patients of the plurality of clinical patients based on comparing the clinical patient embedding and at least one of the compound embedding, the preclinical model embedding, the gene embedding, or the additional clinical patient embedding.

17. A non-transitory computer-readable medium storing instructions that, when executed by at least one processor, cause a computing device to:

generate a multi-entity graph representation comprising nodes and edges by:

generating a first plurality of nodes for a plurality of clinical patients from a digital clinical dataset;

generating a second plurality of nodes for a plurality of genes;

generating a third plurality of nodes comprising at least one of: compound nodes for a plurality of compounds or preclinical model nodes for a plurality of preclinical models from a digital preclinical-model dataset; and generating a plurality of edges by encoding relationships between the nodes into the edges, wherein generating the plurality of edges comprises generating a gene-gene edge between gene nodes of the second plurality of nodes representing genes from cells exposed to a perturbation by:

generating, utilizing a machine learning model, functional response machine learning embeddings for genes corresponding to the gene nodes, the functional response machine learning embeddings comprising one or more phenomic embeddings or transcriptomic embeddings; and generating the gene-gene edge between the gene nodes by determining a similarity measure between the functional response machine learning embeddings;

generate, utilizing a graph neural network and from the multi-entity graph representation, embeddings in a shared latent space, wherein the embeddings comprise a clinical patient embedding and at least one of: a compound embedding, a preclinical model embedding, a gene embedding, or an additional clinical patient embedding; and compare the clinical patient embedding and at least one of the compound embedding, the preclinical model embedding, the gene embedding, or the additional clinical patient embedding to determine a therapeutic treatment for one or more patients of the plurality of clinical patients.

18. The non-transitory computer-readable medium of claim 17, further comprising instructions that, when executed by the at least one processor, cause the computing device to generate the plurality of edges by generating at least one of:

a patient-patient edge between a first patient node and a second patient node of the first plurality of nodes; or a patient-gene edge between a patient node of the first plurality of nodes and a gene node of the second plurality of nodes.

19. The non-transitory computer-readable medium of claim 17, further comprising instructions that, when executed by the at least one processor, cause the computing device to generate the plurality of edges by generating at least one of:

the gene-gene edge between gene nodes of the second plurality of nodes by generating an edge between a first gene node and a second gene node of the second plurality of nodes;

a gene-compound edge between a gene node of the second plurality of nodes and a compound node of the third plurality of nodes; or a preclinical model-gene edge between a preclinical model node of the third plurality of nodes and a gene node of the second plurality of nodes.

20. The non-transitory computer-readable medium of claim 17, further comprising instructions that, when executed by the at least one processor, cause the computing device to determine the therapeutic treatment by determining a patient stratification of the one or more patients of the plurality of clinical patients based on comparing the clinical patient embedding and at least one of the compound embedding, the preclinical model embedding, the gene embedding, or the additional clinical patient embedding.

* * * * *